(12) United States Patent
Kim et al.

(10) Patent No.: US 8,030,048 B2
(45) Date of Patent: Oct. 4, 2011

(54) ENANTIOSELECTIVE EPOXIDE HYDLROLASE AND METHOD FOR PREPARING AND ENANTIOPURE EPOXIDE USING THE SAME

(75) Inventors: Sang-Jin Kim, Kyunggido (KR); Sung-Gyun Kang, Kyunggido (KR); Young-Ok Hwang, Kyunggi-Do (KR); Jung-Hee Woo, Kyunggi-Do (KR); Jang-Cheon Cho, Seoul (KR); Ji-Hyun Kang, Kyunggi-Do (KR); Kae-Kyoung Kwon, Kyunggi-Do (KR)

(73) Assignee: Korea Ocean Research and Development Institute, Kyunggido (KR)

( * ) Notice: Subject to any disclaimer, the term of this patent is extended or adjusted under 35 U.S.C. 154(b) by 635 days.

(21) Appl. No.: 12/089,422

(22) PCT Filed: Oct. 4, 2006

(86) PCT No.: PCT/KR2006/004003
§ 371 (c)(1),
(2), (4) Date: Apr. 7, 2008

(87) PCT Pub. No.: WO2007/043777
PCT Pub. Date: Apr. 19, 2007

(65) Prior Publication Data
US 2010/0120102 A1     May 13, 2010

(30) Foreign Application Priority Data

Oct. 7, 2005   (KR) .................. 10-2005-0094580
Oct. 2, 2006   (KR) .................. 10-2006-0097390

(51) Int. Cl.
*C12N 9/14*     (2006.01)
(52) U.S. Cl. ..................... 435/195; 435/123
(58) Field of Classification Search .......... 435/195, 435/123
See application file for complete search history.

(56) References Cited

OTHER PUBLICATIONS

Morisseau C. et al., Purification and characterization of a hightly enantioselective epoxide hydrolase from *Aspergillus niger*, in Eur J. Biochem, 1999, vol, 263 (2), pp. 386-395 See the abstract and Figs 1-3.
Rink R. at al. Primary structure and catalytic mechanism of the epoxide hydrolase from *Agrobacterium radiobacter* AD1, in J. Bio.. Chem., 1997, vol. 272(23), pp. 14650-14657 See the abstract, Figs 2-3 and Table 1.
NCBI GenBank Accession No. YP_457985 Hypothetical Protein ELI-05480 [*Erythrobacter litoralis* HICC2594] Mar. 30, 2006.
NCBI GenBank Accession No. YP_458376 Probably epoxide Hydrolase [*Erythrobacter litoralis* HTCC2594] Mar. 30, 2006.
NCBI GenBank Accession No. ABC63553 Possible Epoxide Hydrolase-related Protein [*Erythrobacter litoralis* HTCC2594] Jan. 27, 2006.
NCBI GenBank Accession No. YP-615140 Epoxide Hydrolase-like Protein [*Sphingopyxis alaskensis* RB2256] May 30, 2006.
NCBI GenBank Accession No. YP-497537 Epoxide Hydrolase-like [*Novoshingobium aromaticivorans* DSM 12444] Mar. 30, 2006.
NCBI GenBank Accession No. ZP-0104743 Putative Epoxide Hydrolase [Rodobacterales bacterium HTCC2654] Jan. 10, 2006.
International Search Report and Written Opinion PCT/KR2006/004003 dated Dec. 22, 2006.

*Primary Examiner* — Tekchand Saidha
(74) *Attorney, Agent, or Firm* — Gifford, Krass, Sprinkle, Anderson & Citkowski, P.C.

(57) ABSTRACT

The present invention relates to enantioselective epoxide hydrolase proteins isolated from marine microorganisms, which has high enantioselectivity to various epoxide substrates, and a method of preparing the epoxides with high enantio-purity by using the epoxide hydrolases. The enantioselective hydrolase protein of the present invention can be applied for the preparation of enantiopure epoxides with high bioactivity at a high yield.

4 Claims, 13 Drawing Sheets

FIG.3A

```
EEH1    ---------------------------------------MSEIRPFVLDVPKADL   16
EPH1    -----------------------------------MAT-HTFAS--P-PTRFTVDIPQSEL   22
hyl1    -------------------------------MSAPFAKFPSSASISPNPFTVSIPDEQL   28
Eph1    ------------------------------------MTS-----AN---IPTPFQVSTAQQDV   19
EPHX1   MWLEILLTSVLGFAIYWFISRDKEETLPLEDGWWGPGTRSAAREDDSIRPFKVETSDEEI   60
Ephx1   MWLELVLASLLGFVIYWFVSRDKEETLPLGDGWWGPGSKPSAKEDESIRPFKVETSDEEI   60
                                                    *   ::  :  :

EEH1    DRLEHR----KLDDTRWPEKEPVDDWS-------QGTPL--AALQDLAA--YWRDGIDWRAGEAK       65
EPH1    DEIHS----RLDKTRWPATEIVPEDGTDDPTAEGLGAGPTLPLMKELAKGWREEDWKKAQDE        80
hyl1    DDIKTIVRLSKIAPPTYESLQADG-------REGITS-EWLTTMRE--KWLSEFDWRPFEAR       80
Eph1    DRMMA----KIRDTRLPTAPIVPGAS-------WDYGIDL--DWLTELHFK--YWANEWSWEETEKR    70
EPHX1   EDIHQ----RIDKTRFTPPLEDSCFH-------YGFNS--NYLKKVIS--YWRNEFDWKKQVEI     109
Ephx1   KDIHQ----RIDNFRASPPLEGSRFH-------YGINS--NYMKKVVS--YWRNEFDWRKQVEI     109
                                                    :  ::  *  **

EEH1    LNALGQFITEIDGLDIHFLHVR-------SKCDDALPLILIHGWPGSVREEFFDVIPLLTEPQ-     120
EPH1    LNTEEHYMVEIEDISIHFLHER-------STRPNAVRLILCHGWPGHFGEFLNVIPLLTEPSD     136
hyl1    LNSFPQFTTEIEGLTIHFAALF-------SEREDAVPIALLHGWPGSFVEFYPILQLEREFYT    136
Eph1    INKYPEERVDIEEISLHFVHIK-------SKQPDAIPLILSHGWPSSFLEFWEVIDELVDPTK    126
EPHX1   LNRYPHEKTKIEGIDIHFIHVKPPQHPAGHTPKPEDMVHGWPGSFYEFYKIIPLLTDPKN      169
Ephx1   LNQYPHEFKTKIEGLDIHFIHVKPPQLPSGRTPKPLIMVHGWPGSFYEFYKIIPLLTDPKS     169
                          *:  :    :  :  *  :  ***  : .  *
```

```
EEH1    ------------NGGSPFDTLSMDAILDNIMLYMIPETGASAARLYWESFAR------------FGEG---   310
EPH1    EAS-------KQAQPTLTRDELYFTCSLYWFTRSIGTSFLPYSLN------PHFTTFLTDSK           345
hy11    KP-------LPSETILEMVSLYWLTESFPRAIHTYRETTPTASAPNGATMLQKEL                   334
Eph1    PRA------PSAPSQVTPNHIVTVTALYFLIGSIHTSFLPYKEYT------LSPMAVAV               345
EPHX1   TEFRYLEDGGLERKFSLDDLITNVMLYWTTGTIISSQRFYKENLGQG------WMTQKHERM            390
Ephx1   SEYFELEDGGLERKFSLDDLLVNIMIYWTTGTIVSSQRYYKENLGQG------IMVHKHEGM            390
                      :  ::        *                                *

EEH1    TVAIPAGVSAFPKELIPAPRKWAERRYADLVYMNECEKGGHFAAWEQPELEAAELRACFS              370
EPH1    YHLPNFALSLYPGEIYCPAERDAKRTG-NLKWLKDAPEGGHFAALEKPDVEVEHLREAFG              404
hy11    YIHKPFGESTFPKDLCPVPRSWIATTG-NIVEFRDHAEGGHFAALERPRELKIDLTAFVE              393
Eph1    GKKRPIGLSIFPAEITQYPRSWVASSC-KLVNYKVHARGGHFAAVDNPGAYVEDIRETIG              404
EPHX1   KVYVPTGFSAFPEELLHTPEKWVREKYPKLISYSYMVRGGHFAAFEEPELIAQDIRKFLS              450
Ephx1   KVFVPTGFSAFPSELIHAPEKWVRVKYPKLIISYSYMERGGHFAAFEEPKLLAQDIRKFVS             450
                  :     *             :******  :.*

EEH1    IMR---      373
EPH1    VMWEK-      409
hy11    QVWQK-      398
Eph1    KNYHSEL     411
EPHX1   VLERQ--     455
Ephx1   LAEIQ--     455
```

FIG.4A

```
EHPX2   VVTVKPRVRLHFVELGSG---PAVCLCHGFPESWYSWRYQIPALAQAGYRVLAMDMKGYGE  298
Ephx2   YVTVKPGIRLHFVEMGSG---PAICLCHGFPESWFSWRYQIPALAQAGFRVLAIDMKGYGD  296
pEHst   MVAVN-GLNMHIAELGQG---PTILFIHGFPELWYSWRHQMVYLAERGYRAVAPDLRGYGD   64
sEHGm   TYEVN-GIKMHVAEKGEG---PVVLFIHGFPELWYSWRHQILSLSLGYRAVAPDLRGYGD   89
ephA    TIKAN-GISLNVAEQGKG---PMVLLCHGFPEGWYSWRHQLEALAAAGYHAVAPDMRGYGK   64
EEH3    RVPAN-GLEFEVAMAGEGD-HIAIMIHGFPELHETSWRHQMPILLAEMGYRVWAPNMRGYGE   69
EEH2    QHFAYDGLIQIAFWTGGKPDARPLLLVHGYPTASWDWHRVWETLGSK-YHLVAPDMIGFGL   72
                  :  :      .   :::  .*   :   *:  :: ::  *.*  *

EHPX2   SSAPPE---LEEYCMEVLCKEMVTFLDKIG---LSQAVEIGHDWGGMLVWYMALFYPERVRA  354
Ephx2   SSSPPE---TEEYAMELICEEMVTFELNKLG---IPQAVEIGHDWAGVLVWNMALFHPERVRA  352
pEHst   TTGAPINDPSKFSIFHLVGDVVALLEAIAPNEDKVFVAHDWGALIAWHICLFRPDKVKA  124
sEHGm   TEARPS---ISSYNCFHIVGDLVALIDSLG---VQQVFLVAHDWGAITGWYLCMFRPDKVKA  145
ephA    SDRPEA---IDQYTILHMVGDLVGVLDAFE---VKDAVIVGHDWGATIAWHTARLRPDRERA  120
EEH3    TTRPTE---VRDYALDHLTQDVAALIDASG---ATKVTLIAHDWGAIAWYFALLKRPLER  125
EEH2    SDKPRS---GYSIHRQADMEVALIDDHLG---IGAFDAIVEHDIYGVSVGQELLARRAERSAA  126
                    :       .       :.    :.  **..:  *  :   :

EHPX2   VASLNTPFIPANPNMSPLESIKANP-VEDIQLYFQEPGVAEAELEQNLSRTEKSLERASD  413
Ephx2   VASLNTPLMPPPNPEVSPMEVIRSIP-VFNYQLYFQEPGVAEAELEKNMSRTFKSFFRTSD  411
pEHst   LVNLSVEYHPRNSNMNPIEGLKALYGEDYICRFQVPGETEAEFAPIGAKSVLKKMLT--  182
sEHGm   YVCISVPLLRRDPNIRTVDGMRALYGDDYYVCRFQRKPGEMEAQMAEVGTEYVIKNILT--  203
ephA    AAILSVPYRPR-SEARPTSVMPQTADAQEYQLYFQEPGVAEAEFERD-PRATIGAMIYGG  178
EEH3    LVIMNVP---HPKVLQFELRRWEQIKKSWYVFFQLPWLPEKRIGADSGKRIG------  175
EEH2    QGIIGQTVFLNGGIFPDQHRPRPIQKLGTSPLGFLVGLLTNREKFGRSFSEVEG------  179
                                           :       :       
```

FIG.4B

```
Ephx2    DMGLLLTVNKAT------------EMGGILVGTPEDPKVSKITTEEEIEYYIQQFKKSGFR  459
pEHst    YRDPAPTYFP--------------KGKGLEAIADAPIVLSTWLSEEELDYYANKFEQTGFT  229
sEHGm    TRNPGPPILP--------------KGR-FQFNPEMPNTLPSWLTEEDLAYYVSKFEKTGFT  249
epHA     SGEGAAAIRASAERAGRTVGVGMVSRKDGMLPKVQVPLPSWLSATDLDYYSAEFARSGFR  238
EEH3     ---------------------------ELEAQTSCNPERFGPDVKAVYAAGAARPGAPR  207
EEH2     ---------------------------PDTQPGAQELDEFWDLVSHNGGNRIM  205

EHPX2    GPLNWYRNMERNWKWACKSLGRKILIPALMVTAEKDFVLVPQ---------MSQHMEDWIPHL  514
Ephx2    GPLNWYRNTERNWKWSCKALGRKILVPALMVTAEKDIVLRPE---------MSKNMENWIPFL  513
pEHst    GALNYYRALSINSELTAPWTGAQVNVPTKFLVGEFDLAYHMRGAKEYIHNGGFKKYVPLL  289
sEHGm    GPINYYRNFNINWELTAPWTGGQIKVPVKYITGELDMVYNSINLKEYIHGGGEKQDVPNL  309
epHA     GPLNYYRNIDRNWELMGAFEGVKVKVVPSIELAGDHDMVIAFPGAAEHLAN--MKQFVPQL  296
EEH3     AMVNYYRAAMRERDTIDPGD-FRVDVPTLLVWGEEDVALNIR--------CTEGTEQWVPDI  260
EEH2     HKLIHYIADRKEHAERMFDALRIAQGDIGIINGALDPVSGRH-------AYEAWRERLPDA  259

EHPX2    KRGHIED-CGHWTQMDKPTEVNQILIKWLDSDARNPPVVSKM  555
Ephx2    KRGHIED-CGHWTQIEKPAEVNQILIKWLKTEIQNPSVTSKI  554
pEHst    EEVVLEGAAHFVNQERPHEISKHLYDEIQKF----------  321
sEHGm    EQVIVQKGVAHHNNQEAAEEIDNYIYDEINKF----------  341
epHA     REIKILPGCGHWTQQERPTEVNAAIVEFLRSLPG--------  330
EEH3     TVKRLPN-VSHWVQQDAPDEVNAILREWLPKPAPAS------  295
EEH2     RHHLIPT-VGHYPQVEDPQTVSRVTIDWLFAR----------  289
```

ENANTIOSELECTIVE EPOXIDE HYDLROLASE AND METHOD FOR PREPARING AND ENANTIOPURE EPOXIDE USING THE SAME

CROSS-REFERENCE TO RELATED APPLICATIONS

This application is the U.S. national phase of PCT/KR2006/004003 filed Oct. 4, 2006, which claims priority of Korean Patent Applications 10-2005-0094580 filed Oct. 7, 2005 and 10-2006-0097390 filed Oct. 2, 2006.

FIELD OF THE INVENTION

The present invention relates to an enantioselective epoxide hydrolase and a method of epoxide having enantiopure activity on various epoxide substrates by using the enantioselective epoxide hydrolase.

BACKGROUND OF THE INVENTION

Many bioactive materials such as medicines are in a form of various enantiomer, and only a specific enantiomer has the desired efficacy, and the remnant enantiomers causes serious undesirable effect. In aspects of safety and bioactivity, only single enantiomer must be produced, and thus many researches on the synthesis of enantio-pure bioactive material can be processed.

Enantiopure epoxides and vicinal diols are versatile synthetic intermediates for the preparation of enantiopure bioactive compounds such as pharmaceutical compounds, pesticides, and functional foods (Grogan, et al., FEMS Microbiol. Lett., 141:239-243, 1996; Arahira, et al., Eur. J. Biochem., 267:2649-2657, 2000), because the compounds has excellent reactivity and can induce the various reactions.

Particularly, the enantiopure epoxides can be prepared by using the chiral chemical catalysts and enzymes, and only single enantiomer is prepared by performing the selective hydrolysis with epoxide hydrolase to each enantiomer in racemic epoxide substrates. The method can be used commercially in the near future, because it can change inexpensive racemic substrate to enantiopure epoxide having higher added value. The epoxide hydrolase hydrolyzes only (R) or (S)-enantiomer among racemic epoxide substrate with enantio-selectivity to diol and leave the other type of enantiomer, so as to produce enantiopure epoxide. In addition, the enantioselectivity of epoxide hydrolase to (R) or (S)-enantiomer depends on microorganisms and substrate structure.

Epoxide hydrolases (EHase; EC 3.3.2.3) are ubiquitous enzymes that have been isolated from a wide variety of sources such bacteria, yeast, fungi, insect, plant and mammalian (Weijers, et al., J. Mol. Catal. B Enzym., 6:199-214, 1999; Archelas, & Furstoss, Curr. Opin. Chem. Biol., 5:112-119, 2001). Due to the potential application in the production of enantiopure epoxides by kinetic resolution of enantioselective EHase, several EHases have been developed (Tokunaga, et al., Science, 277:936-938, 1997).

However, the limited number of enantioselective EHases demands studies to explore new enantioselective EHases for the production of enantiopure epoxides in pharmaceutical industries.

Most EHases are members of the α/β hydrolase family which includes proteases, lipases, esterases, dehalogenases, and peroxidases (Nardini, & Dijkstra, Curr. Opin. Struct. Biol., 9:732-737, 1999; Rick, et al., J. Am. Chem. Soc., 121: 7417-7418, 1999). α/β domains consist of a central, parallel or mixed β sheet surrounded by α helices. These enzymes characteristically employ a two-step mechanism in which a catalytic nucleophile of the enzyme attacks a polarized electrophile substrate of the covalent intermediate subsequently hydrolyzed (Yamada, et al., J. Biol. Chem., 275:23082-23088, 2000). The conserved catalytic triad of α/β hydrolase fold enzymes consists of a nucleophilic residue (Asp or Ser), an acidic residue (Asp or Glu) and a conserved histidine residue. The nucleophile fits the conserved amino-acid-sequence motif, Sm-X-Nu-Sm (Sm=small residue, X=any residue and Nu=nucleophile). Another conserved amino acid sequence is the HGXP motif containing the oxyanion hole of the enzyme (Ollis, et al., Protein Eng., 5:197-211, 1992).

However, the conservation in the primary sequence among EHases is limited only in 2 or 3 amino acids of the critical regions, leading to make the screening by homology search difficult.

SUMMARY OF THE INVENTION

The present inventor found the epoxide hydrolase having high enantioselective hydrolyzing activity by screening *Erythrobacter* sp., *Sphingopyxis* sp., *Novosphingobium* sp. and *Rhodobacterium* sp. from various marine environments, analyzing the ORF sequence in their genome to determine a candidate gene, and expressing the candidate gene.

The object of the present invention is to provide enantioselective epoxide hydrolase proteins which produce high enantiopure epoxide and are isolated from marine environments.

The further object of the present invention is to provide a method of preparing enantiopure epoxide by using the epoxide hydrolase proteins having high enantio-selectivity to various epoxide substrates.

Another object of the present invention is to provide *Erythrobacter* sp., *Sphingophyxis* sp., *Novosphingobium* sp., and *Rhodobacterium* sp. with enantioselective hydrolase activity from the various marine environments and a method of screening them.

To achieve the object, the present invention provide an enantioselective epoxide hydrolase protein which is isolated from *Erythrobacter litoralis*, and has the following characteristics: 1) a molecular weight of 30 to 45 kDa as measured by SDS-PAGE method; 2) an optimum pH 6.5 to 8.0; and 3) an optimum temperature of 40 to 60° C. Preferably, the protein comprises an amino acid sequence as shown in SEQ ID NO: 13, an amino acid sequence as shown in SEQ ID NO: 15, or an amino acid sequence as shown in SEQ ID NO: 17. More preferably, the amino acid sequence as shown in SEQ ID NO: 13 is coded by a nucleotide sequence as shown in SEQ ID NO: 14, the amino acid sequence as shown in SEQ ID NO: 15 is coded by a nucleotide sequence as shown in SEQ ID NO: 16, and the amino acid sequence as shown in SEQ ID NO: 17 is coded by a nucleotide sequence as shown in SEQ ID NO: 18.

In addition, the present invention an enantioselective epoxide hydrolase protein which is isolated from *Sphingophyxis alaskensis*, and has the following characteristics: 1) a molecular weight of 45 to 50 kDa as measured by SDS-PAGE method; 2) an optimum pH 7.0 to 8.0; and 3) an optimum temperature of 30 to 40° C. Preferably, the protein has an amino acid sequence as shown in SEQ ID NO: 28, and more preferably, is coded by a nucleotide sequence as shown in SEQ ID NO: 29.

In another aspect, the present invention an enantioselective epoxide hydrolase protein which is isolated from *Novosphingobium aromaticivorans*, and has the following characteristics: 1) a molecular weight of 40 to 45 kDa measured by SDS-PAGE method; 2) an optimum pH 7.0 to 8.0; and 3) an optimum temperature of 30 to 40° C. Preferably, the protein has an amino acid sequence as shown in SEQ ID NO: 30, and more preferably, is coded by a nucleotide sequence as shown in SEQ ID NO: 31.

In further aspect, the present invention provides an enantioselective epoxide hydrolase protein which is isolated from *Rhodobacterium* sp. HTCC2654, and has the following characteristics: 1) a molecular weight of 35 to 40 kDa measured by SDS-PAGE method; 2) an optimum pH 7.0 to 8.0; and 3) an optimum temperature of 30 to 40° C. Preferably, the protein has an amino acid sequence as shown in SEQ ID NO: 32, and more preferably is coded by a nucleotide sequence as shown in SEQ ID NO: 33.

In still further aspect, the present invention provides a method of preparing enantiopure epoxide by using enantioselective epoxide hydrolase protein.

BRIEF DESCRIPTION OF THE DRAWING

A more complete appreciation of the invention, and many of the attendant advantages thereof, will be readily apparent as the same becomes better understood by reference to the following detailed description when considered in conjunction with the accompanying drawing.

FIG. 3A to 3C show alignment between amino acid sequence of purified EEH1 protein to that of known protein where EEH1 is represented by SEQ ID NO: 13, EPH1 (*Rhodotorula glutinis*) is represented by SEQ ID NO: 34, hyl1 (*Aspergillus niger*) is represented by SEQ ID NO: 35, Epb1 (*Xanthophyllomyces dendrorhous*) is represented by SEQ ID NO: 36, EPHX1 (*Homo sapiens*) is represented by SEQ ID NO: 37, and Ephx1 (*Rattus norvegicus*) is represented by SEQ ID NO: 38;

FIG. 4A and 4B show alignment between amino acid sequence purified from EEH1 and EEH2 to that of known protein, where EHPX2 (*Homo sapiens*) is represented by SEQ ID NO: 39, Ephx2 (*Rattus norvegicus*) is represented by SEQ ID NO: 40, pEHSt (*Solanum tuberosum*) is represented by SEQ ID NO: 41, sEHGm (Glycine max) is represented by SEQ ID NO: 42, ephA (*Bradyrhizobium japonicum*) is represented by SEQ ID NO: 43, EEH3 is represented by SEQ ID NO: 17, and EEH2 is represented by SEQ ID NO: 15;

DETAILED DESCRIPTION AND THE PREFERRED EMBODIMENTS

Figure 1A:
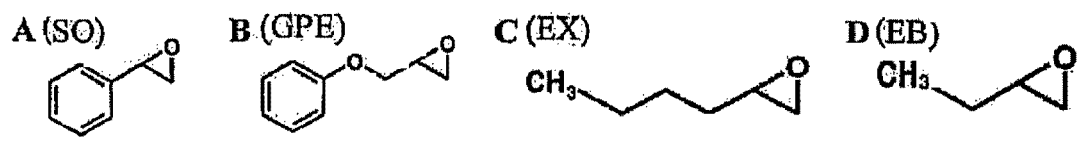
FIG. 1A shows the type of various epoxide substrates, wherein A, B, C and D indicate styrene oxide(SO), glycidyl phenyl ether(GPE), 1,2-epoxyhexane(EX) and 1,2-epoxybutane(EB), respectively.

The present invention will now be explained in more detail.

The present invention provides purified enantioselective epoxide hydrolase proteins from *Erythrobacter litoralis,Sphingophyxis alaskensis,Novosphingobium aromaticivorans* and *Rhodobacterium*.

*Erythrobacter* sp., *Sphingopyxis* sp., *Novosphingobium* sp. and *Rhodobacterium* sp. are selected by screening, and then ORF sequence in their genome are aligned to select a candidate gene. The enantioselective hydrolase proteins having high enantioselectivity to the various substrates are separated and purified from the expressed products from the candidate genes. More specifically, the enantioselective hydrolase having high enantio-selectivity are separated by using the following screening method from the microorganisms including *Erythrobacter* sp., *Sphingophyxis* sp., *Novosphingobium* sp., and *Rhodobacterium* sp. which are obtained from various marine environments. The screening method includes the steps of:

1) preparing a sample of interest from various marine environments;

2) selecting a positive strain by culturing the sample in enriched medium;

3) determining a candidate gene by analyzing the ORF nucleotide sequence in genome of the strain, and aligning the obtained nucleotide sequence with the nucleotide sequence of known epoxide hydrolase; and 4) detecting the epoxide hydrolase having high enantioselective hydrolyzing activity from the candidate gene by introducing the candidate gene to expression vector and culturing the vector.

The sample of interest in step 1 of the screening method is not limited particularly, but can be marine sediment, sponge and algae which are collected from various marine environments such as Hoogin in Gangwon-Do, Ulleungdo (Island), Dokdo (Island), Taejongdae in Busan, and Sihwa in Gyeonggi-do in Republic of Korea, and Kagoshima in Japan. The strains can be isolated from the collected marine sediment directly, or after culturing the marine sediment in enriched medium.

The enriched medium step 2 in the screening method, the enriched medium is not limited particularly, preferably 1 wt % of styrene oxide (SO) or alkan mixture (nC8, C10, nC12, nC13, nC14, nC15, nC16, C17, nC18, and cyclohexan (Sigma, Mo., USA) are mixed in 1 L of mineral salt medium (MM 2) of sea water.

In the screening method, the bacteria in step 3) is selected from *Erythrobacter litoralis, Erythrobacter* sp. 2216.25.25, *Erythrobacter aquimaris* SW-110, *Erythrobacter gaetabuli, Alterierythrobacter epoxidivorans,Erythrobacter luteolus* SW-109, *Erythrobater* sp. MBIC3031 and *Erythrobacter longus*. The microorganism can be *Erythrobacter* sp. selected from the group consisting of *Erythrobacter litoralis* HTCC2594, *Erythrobacter* sp. AKS329, *Erythrobacter* sp. *aquimaris* JCS325, *Erythrobacter gaetbuli* JCS340 JCS325, *Erythrobacter* sp. JCS340, *Erythrobacter* sp. JCS350, *Erythrobacter* sp. JCS358, *Alterierythrobacter* sp. JCS350, *Erythrobacter aquimaris* sp. JCS360, *Erythrobacter aquimaris* sp. JCS364, *Erythrobacter luteolus* sp. JCS368, *Erythrobacter* sp. HJ239, *Erythrobacter longus* sp. DokDo 15, *Erythrobacter litoralis* DMS8509 and *Erythrobacter geatbuli* KCTC12227 (Table 2), but not limited thereto.

The open reading frame analysis can be carried out by ProteinFinder produced by Ensoltek (Yuseong-gu, Daejeon, Korea) and BLAST program, but not limited thereto. In addition, analyzing method of amino acid sequence of conventional epoxide hydrolase, and the new epoxide hydrolases of the present invention can be preformed by using CLUSTAL W program(Thompson, et al., Nucleic. Acids. 22:4673-4680, 1994), but not limited thereto.

The candidate genes in step 3) include EEH1 gene represented by SEQ ID NO: 13, EEH2 gene represented by SEQ ID NO: 16 and EEH3 gene represented by SEQ ID NO: 18 from *Erythrobacter litoralis* HTCC2594, sEEH gene represented by SEQ ID NO: 29 from *Sphingophyxis alaskensis*, nEEH gene represented by SEQ ID NO: 31 from *Novosphingobium aromaticivorans*, and rEEH gene represented by SEQ ID NO: 33 from *Rhodobacterium*, but not limited thereto. In addition the candidate gene can be entire open reading frame or its fragment derived from the genes.

In step 4 of the screening method, the expression vector can be any expression vector used in the prior art, for example pET-24a(+).

In step 4, analysis of the hydrolyzing activity to the various epoxide substrates was performed by a spectrophotometric assay based on the epoxide extracted from the reaction mixture and spectrophotometric quantification of the non-extracted diol or gas chromatography.

After four (4) candidate strains are screened from marine environment, epoxide hydrolase proteins having high enantioselective hydrolyzing activity to various epoxide substrates are separated and purified from the candidate strains. The epoxide hydrolase are separated and purified by general separation and purification method used generally in this field. For example, after performing seed culture in LB medium enriched with Kanamycin (50 ug/ml), 1% of the cultured strain is added to the main medium, cultured for 3 hours, and added with IPTG to 1 mM of the final concentration. To purify the expressed gene product, His-Tag is added to the candidate gene, and then is cleaved by Talon resin (Clontech, Co.).

Figure 9:
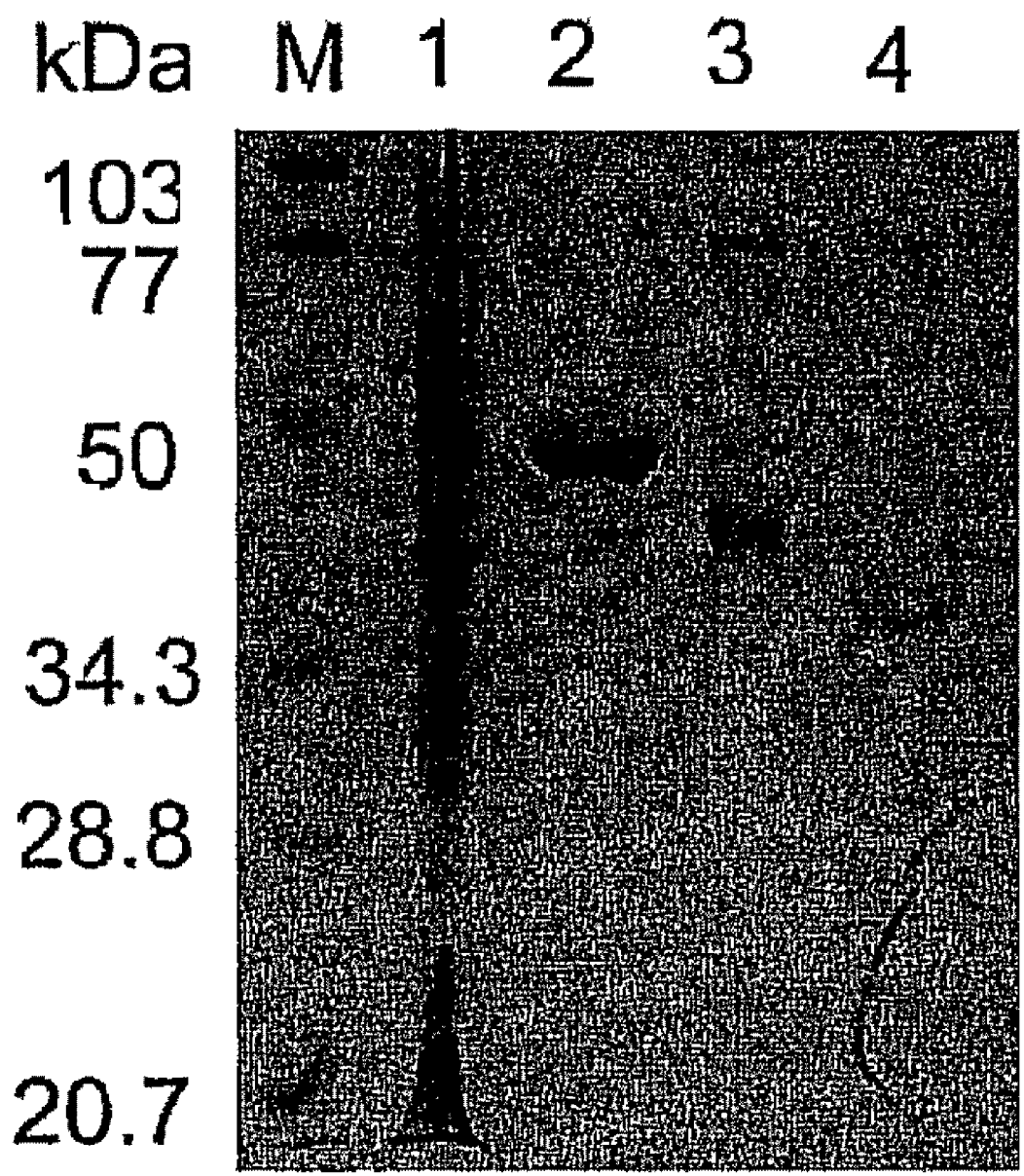
FIG. 9 shows the purity of EHase isolated from *Novosphingobium aromativorans* with SDS-PAGE.

In addition, by analyzing ORF sequence in genome DNA to in order to analyze the gene encoding the purified epoxide hydrolase protein, 1.122 bp gene (EEH1, SEQ ID NO: 14), 870 bp gene (EEH2, SEQ ID NO: 16) and 888 bp gene (EEH3, SEQ ID NO: 18) are isolated from *Erythrobacter litoralis* HTCC2594.

sEEH gene (SEQ ID NO: 29) of *Sphingophyxis alaskensis*, nEEH gene (SEQ ID NO: 31) of *Novosphingobium aromaticivorans*, and rEEH gene (SEQ ID NO: 33) of *Rhodobacterium* sp. HTCC2654 are separated respectively. In addition, each gene is introduced into expression vector, pET-24a (+), transformed to BL21-CodonPlus (DE3)-RP (Novagen), and then performed by SDS-PAGE electrophoresis. As a result, the hydrolases are 41 kDa-sized protein (rEEH1, SEQ ID NO: 13) isolated from *Erythrobacter litoralis* HTCC2594, 33.4 kDa-sized protein (rEEH2, SEQ ID NO: 15) and 34.5 kDa-sized protein (rEEH3, SEQ ID NO: 17), 49 kDa-sized protein (sEEH, SEQ ID NO: 28) isolated from *Sphingophyxis alaskensis*, 43 kDa-sized protein (nEEH, SEQ ID NO: 30) isolated from *Novosphingobium aromaticivorans*, and 36 kDa43 kDa-sized isolated from *Sphingophyxis alaskensis* (rEEH, SEQ ID NO: 32) isolated from *Rhodobacterium* sp. HTCC2654 (FIG. 9).

The present invention provides an enantioselective epoxide hydrolase protein which is isolated from *Erythrobacter litoralis* HTCC2594, and has the following characteristics:

1) a molecular weight of 30 to 45 kDa measured by SDS-PAGE method;
2) an optimum pH of 6.5 to 8.0; and
3) an optimum temperature of 40 to 60° C.

Preferably, the rEEH1, rEEH2 and rEEH3 hydrolase isolated from *Erythrobacter litoralis* has a molecular weight of 41 kDa (polypeptide as shown in SEQ ID NO: 13), 33.4 kDa (polypeptide as shown in SEQ ID NO: 15) and 34.5 kDa (polypeptide as shown in SEQ ID NO: 17) (FIG. 6A and FIG. 6B), optimum pH of 6.5(rEEH1), 7.5(rEEH2) and 8.0 (rEEH3)(FIG. 7A), and optimum temperature of 50° C. (rEEH1), 55° C. (rEEH2) and 45° C. (rEEH3)(FIG. 7B), respectively.

The present invention provides an enantioselective epoxide hydrolase protein which is isolated from *Sphingophyxis alaskensis*, and has the following characteristics:

1) a molecular weight of 45 to 50 kDa measured by SDS-PAGE method;
2) an optimum pH of 7.0 to 8.0; and
3) an optimum temperature of 30 to 40° C.

Preferably, the rEEH hydrolase has a molecular weight of 49 kDa (polypeptide as shown in SEQ ID NO: 28) (see FIG. 9), optimum pH of about 7 and optimum temperature of 30-40° C.

The present invention provides an enantioselective epoxide hydrolase protein which is isolated from *Novosphingobium aromaticivorans*, and has the following characteristics:

1) a molecular weight of 40 to 45 kDa measured by SDS-PAGE method;
2) an optimum pH of 7.0 to 8.0; and
3) an optimum temperature of 30 to 40° C.

Preferably, the rEEH hydrolase has a molecular weight of 43 kDa (polypeptide as shown in SEQ ID NO: 30)(see FIG. 9), optimum pH of 7.0-8.0 and optimum temperature of 30-40° C.

The present invention provides an enantioselective epoxide hydrolase protein which is isolated from *Rhodobacterium* sp. HTCC2654, and has the following characteristics:

1) a molecular weight of 35 to 40 kDa measured by SDS-PAGE method;
2) an optimum pH 7.0 to 8.0; and
3) an optimum temperature of 30 to 40° C.

Preferably, the rEEH hydrolase has a molecular weight of 36 kDa (polypeptide as shown in SEQ ID NO: 32) (see FIG. 9), an optimum pH 7.0 to 8.0; and an optimum temperature of 30 to 40° C.

In another aspect of the present invention, a method of preparing epoxides with high enantiopure by using the enantioselective epoxide hydrolase protein having a high enantioselectivity on various epoxide substrates.

In an embodiment, 2-100 mM racemic styrene oxide can be reacted with purified enzymes such as EEH1, EEH2, EEH3, sEEH, nEEH, and rEEH, recombinant *E. coli* or wild type strain in each optimum condition (as confirmed by Gas Chromatography), and then the produced epoxide are used.

In the present invention, the substrates of enantioselective epoxide hydrolase can not be limited particularly, and the examples are styrene oxide (SO), glycidyl phenyl ether (GPE), epichlorohydrin (ECH), epifluorohydrin (EF), 1,2-epoxybutane (EB) and 1,2-epoxyhexane (EX).

The hydrolase has an amino acid sequence as shown in SEQ ID NO: 13, an amino acid sequence as shown in SEQ ID NO: 15, or an amino acid sequence as shown in SEQ ID NO: 17. The preparation method can be performed at pH 6.5 to 8.0 and temperature of 40 to 60° C.

The hydrolase has an amino acid sequence as shown in SEQ ID NO: 28, an amino acid sequence as shown in SEQ ID NO: 30, or an amino acid sequence as shown in SEQ ID NO: 32. The preparation method can be performed at pH 7.0 to 8.0 and temperature of 30 to 40° C.

Practical and presently preferred embodiments of the present invention are illustrative as shown in the following Examples. However, it will be appreciated that those skilled in the art, on consideration of this disclosure, may make modifications and improvements within the spirit and scope of the present invention.

EXAMPLE 1

Screening Enantioselective Epoxide Hydrolase(EHase)-Producing Microorganisms

<1-1> Materials and Reagents

The epoxides used in the present invention are indicated in FIG. 1. Wherein, racemic styrene oxide was purchased from Fluka Co., and pure (R)-styrene oxide, pure (S)-styrene oxide, and all other racemic epoxides were purchased from Aldrich Co, respectively. The chiraldex gamma-cyclodextrin trifluoroacetyl(G-TA) capillary GC column was purchased from Astec Co. (Whippany, N.J.), and other medium components were purchased Merck and Difco Co.

<1-2> Sample Preparation

Marine sediment, sponge and algae samples were collected from Hujin (depth, ~20 m; 37° 51' N, 129° 45' E), Ulleungdo (depth, ~758.7 m; 38° 00' N, 131° 27' E), Dokdo (depth, ~620 m; 37° 14' N, 131° 45' E), Taejongda (depth, ~20 m; 35° 14' N, 129° 45' E), Sihwa (Yellow sea, Korea), and Kagoshima bay (depth, 100~200 m; 31° 90' N, 130° 48' E). Wherein, the sediment samples were collected using various method such as grab, core sampler, and scuba diving. Immediately after sampling, 0.3 g of chilled sediment was ground in a mortar, and incubated in the nutrition abundant culture media. Samples were collected under formal agreement with all legal parties.

<1-3> Strain Isolation

To make the nutrition abundant culture media, 1% of SO substrate, epichlorohydrin, or alkane mixture ($nC_8$, $nC_{10}$, $nC_{12}$, $nC_{13}$, $nC_{14}$, $nC_{15}$, $nC_{16}$, $nC_{17}$, $nC_{18}$, and cyclohexane, Sigma Chemical Co., St Louis, Mo., USA) was mixed with 1 liter of seawater of mineral salt medium (MM2)(Ferrara-Guerrero et al., Handbook of methods in microbial ecology. Lewis Publishers, Florida and p 9-19, 1993). 7 days after incubation at 25° C., clones were isolated. The isolates were purified through successive inoculation and incubation on ZoBell agar at 25° C. The isolated strains were used in the following screening step.

<1-4> Strain Culture

*Erythrobacter litoralis* HTCC2594 was cultured in ZoBell 2216E broth (Oppenheimer & Zobell, 1952) medium consisting of 0.5% peptone, 0.1% yeast extract, and 75% seawater (pH 7.5) at 30° C. for 1 day. *Sphingopyxis alaskensis* and *Novosphingobium aromaticivorans* were cultured in nutrient medium consisting of 0.5% peptone and 0.3% yeast extract at 30° C. *Rhodobacterium* sp. HTCC2654 was cultured in marine broth 2216(Difco) medium at 25° C. The bacterial cells were suspended in ZoBell 2216E broth medium containing 20% glycerol, and stored at −80° C. until used. *E. coli* DH5α and *E. coli* BL21-CodonPlus (DE3)-RIL cells (Stratagene, LaJolla, Calif.) were used for plasmid propagation and gene expression, respectively. The cells were cultured in Luria-Bertani(LB) broth medium containing appropriate antibiotics at 37° C.

<1-5> Identification of an EHase-Producing Strain

With the method as described above, an embodiment of the present invention isolated total 181 strains from marine environments. Among 181 strains, 31 stains were shown to hydrolyze SO substrate by spectrophotometric measurement (Table 1). After analyzing the hydrolyzing activity of enantioselective EHase of the strains with gas chromatography(GC), final 1 strain, JCS358 was shown to preferentially hydrolyze (R)-epoxide of SO (Table 1 and FIG. 1B).

TABLE 1

Screening of an enantioselective EHase-producing marine microorganism and the sequence analysis of 16S rRNA gene from the microorganism

| Sampling site | Strains | The phylogenetic grouping of the strains (number/%) | Screening Diol assay | Screening GC analysis |
|---|---|---|---|---|
| Hujin | 64 | (-pro[a]: 4 (6.25%) (-pro[b]: 47 (73.4%) G.P.[c]: 4 (6.25%) CFB[d]: 9 (14.1%) | 18 | 0 |
| Uleungdo | 9 | (-pro: 3 (33.3%) G.P.: 6 (66.7%) | 3 | 0 |
| Dokdo | 9 | (-pro: 3 (33.3%) (-pro: 2 (22.2%) G.P.: 3 (33.3%) CFB: 1 (11.1%) | 2 | 0 |
| Taejongdae | 18 | (-pro: 8 (44.4%) (-pro: 6 (33.3%) G.P.: 2 (11.1%) CFB: 2 (11.1%) | 8 | 0 |
| Sihwa | 15 | (-pro: 3 (20%) (-pro: 8 (53.3%) G.P.: 2 (13.3%) CFB: 2 (13.3%) | 0 | 0 |
| Kagoshima, Japan | 66 | (-pro: 26 (39.4%) (-pro: 13 (19.7%) G.P.: 21 (31.8%) CFB: 6 (9.1%) | — | 1 |
| Total | 181 | (-pro: 44 (24.4%) (-pro: 79 (43.6%) G.P.: 38 (21.0%) CFB: 20 (11.0%) | 31 | 1 |

[a]α-pro: α-proteobacteria;
[b]γ-pro: γ-proteobacteria;
[c]G.P.: Gram-positive;
[d]CFB: Cytophaga-Flavobacteria-Bacteroides <1-6> Sequence Analysis of 16S rRNA from JCS358 Strain An embodiment of the present invention was performed by the sequence analysis of 16S rRNA gene on the genomic DNA sequence of the strain. The 16S rRNA gene was amplified from genomic DNA by PCR (Weisburg, et al., J. Bacterioaol., 173: 697-703, 1991) using the SEQ ID NO: 2(5'-AGAGTTTGATCATGGCTCAG-3', 27F) and SEQ ID NO: 3(5'-AAGGAGGTGATCCAGCCGCA-3', 1518R). DNA sequencing was performed with the automated sequencer (ABI 3100) using a BigDye terminator kit (PE Applied Biosystems, Foster City, Calif.).

The results indicated that the JCS358 strain belonged to *Erythrobacter* spp. with 98% similarity to *Erythrobacter gaetbuli*(Table 2). Because the *Erythrobacter* spp. was known to an aerobic heterotrophic α-proteobacteria, generally found in a variety of marine environments such as sea water, sediment and tidal flat, to examine whether the activity of enantioselective hydrolysis of the strain toward epoxide substrate is commonly found in *Erythrobacter* spp., an embodiment of the present invention was examined the hydrolyzing activity for 9 additional *Erythrobacter* strains isolated from various marine environments, wherein the strains were stocked in KORDI collection or acquired from culture collections (Anzai, et al., Int. J. Syst. Evol. Microbiol., 50: 1563-1589, 2000; Denner, et al., Int. J. Syst. Evol. Microbiol., 52: 1655-1661, 2002; Shiba & Simidu, Int. J. Syst. Bacteriol., 32: 211-217, 1982; Yoon, et al., Int. J. Syst. Evol. Microbiol., 53: 1169-1174, 2003 and Yurkov, et al., Int. J. Syst. Bacteriol., 44: 427-434, 1994).

As shown in Table 2, 7 strains out of 10 strains (AKS 329, JCS 325, JCS 340, JCS 350, JCS 358, JCS 360 and JCS 364) displayed ee value of high enantioselective hydrolyzing activity toward SO substrate. In the 7 *Erythrobacter* strains, the kinetic preference of the EHase of the strains was mostly toward (R)-SO. These results indicate that *Erythrobacter* spp. could metabolize epoxide substrates and be valuable to fine novel enzymes related with epoxide.

follows. 0.2 g of whole cells having EHase activity measured by spectrophotometer were mixed with 2 mM of SO in a 10 ml vial containing 1 ml of Tris-HCl (100 mM, pH 8.0), and incubated for 15 h at 30° C. After extracting the reaction mixtures with 2 ml of hexane, and then the extracts were analyzed on a chiraldex gamma-cyclodextrin trifluoroacetyl column (0.25 mm ID, 30 m length; Astec, Adv., Tech., USA; van Loo et al., 2004) using a GC system equipped with FID detector (Hewlett-Packard, Avondale, Pa., USA).

The temperatures of oven, injector and detector in GC analysis for racemic SO were 90° C., 220° C. and 230° C., respectively. The hydrolysis toward other epoxide substrates depicted in FIG. 1A was also analyzed with the method as described above.

Figure 1B:
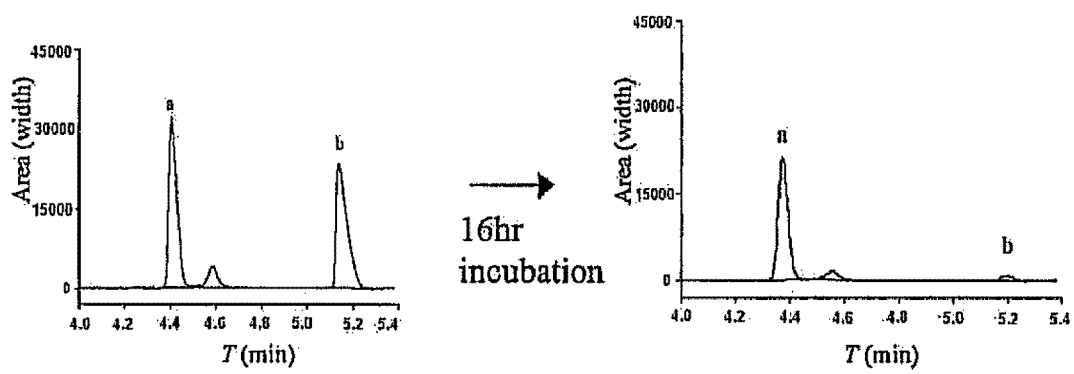
FIG. 1B shows the hydrolyzing activity of *Erythrobacter* spp. JCS358 toward the racemic SO substrate with gas chromatography(GC), wherein A and B indicate (S)-styrene oxide and (R)-styrene oxide, respectively.

The results of the hydrolyzing activity of the 10 strains toward various epoxide substrates depicted FIG. 1A were

TABLE 2

The activities of enantioselective EHase of *Erythrobacter* spp. toward various epoxide substrates

| Strain name | Best-matched neighbor | Similarity (%) | ee$^a$ (%)/abs. conf.$^b$ | | | |
|---|---|---|---|---|---|---|
| | | | SO | GPE | EX | EB |
| AKS 329 | *Erythrobacter* sp. 2216.25.25 | 99 | 96.4/S | 99/R | 47.5/S | 19.6/R |
| JCS 325 | *Erythrobacter aquimaris* SW-110 | 99 | 99/S | 8.15/RA D$^c$ | 64.8/S | 37.2/R |
| JCS 340 | *Erythrobacter gaetbuli* | 99 | 80.9/S | 62.2/RA D | 81.3/S | 23.8/R |
| JCS 350 | *Alterierythrobacter epoxidivorans* | 97 | 80.6/S | 99/R AD | 99/S | 11.5/R |
| JCS 358 | *Erythrobacter gaetbuli* | 98 | 99/S | 81.7/R | 72.5/S | 5.5/R |
| JCS 360 | *Erythrobacter aquimaris* SW-110 | 99 | 99/S | 99/R AD | 28.0/S AD | 20.6/R |
| JCS 364 | *Erythrobacter aquimaris* SW-110 | 99 | 99/S | 99/R AD | 37.4/S AD | 34.6/R |
| JCS 368 | *Erythrobacter luteolus* SW-109 | 99 | 2.8/S X$^d$ | 5.5/S | 26.0/S | 14.2/R |
| HJ 239 | *Erythrobacter* sp. MBIC 3031 | 99 | 0.09/S X | X | 2.7/S X | ND$^e$ |
| DokDo 15 | *Erythrobacter longus* | 99 | 5.0/S X | 12.4/R | 13.3/S | 7.98/R |

$^a$ee (%): enantiomeric excess,
$^b$abs. Conf.: absolute configuration, meaning remaining epoxide after incubation,
$^c$AD: hydrolyzed (S)- and (R)-enantiomers,
$^d$X: not detected an EHase activity,
$^e$ND: not determined.

<1-7> Analysis of the Hydrolyzing Activity of *Erythrobacter* Spp. Toward Various Epoxide Substrates EHase activity of the strains was measured by a spectrophotometric assay based on the epoxide extracted from the reaction mixture and spectrophotometric quantification of the non-extracted diol (Bhatnagar, et al., J. Biochem. Biophys. Methods., 50:1-13, 2001). The isolated strains were shake-cultured in a flask containing 30 ml of ZoBell medium at 25° C. 24 h after incubation, the supernatant was removed by centrifugation at 4,300×g for 20 min at 4° C. The whole cells were washed twice with 10 mM of sodium phosphate buffer (pH 6.8), and 4 mM of SO containing dimethyl formamide (DMF) was mixed with 0.04 g of whole cells which were resuspended in 10 mM of sodium phosphate buffer (pH 6.8), and the mixture was incubated at 30° C. for 15 min. Then, 40 ul of the NaIO$_4$ stocked solution (stocked with 200 mM of NaIO$_4$ in DMF) was added, and immediately vortexed for 2 min. After centrifugation at 16,500×g for 90 sec, the supernatant was quantified by spectrophotometric measurement at 290 nm.

Also, the measurement of enantioselective EHase activity was executed by a gas chromatography (GC) analysis as shown to Table 2, indicating that the 7 *Erythrobacter* strains could hydrolyze preferentially (S)-GPE with variation at ee value, which is opposite to the enantioselective hydrolytic activities toward SO. In contrast to SO and GPE, both (R)- and (S)-epoxide of 1,2-epoxyhexane(EX) and 1,2-epoxybutane(EB) were hydrolyzed by most of strains (Table 2).

<1-8> Kinetic resolution of racemic SO by *Erythrobacter* sp. JCS 358

Kinetic resolution of 2 mM of racemic SO was examined in a batch mode at 30° C. using a *Erythrobacter* spp. JCS 358 strain. Initial concentration of racemic SO was 2 mM, and 0.2 g of whole cells were used. 24 h after incubation, the reaction mixtures were removed periodically, and the residual epoxides were analyzed by GC after extraction with hexane.

Figure 2:
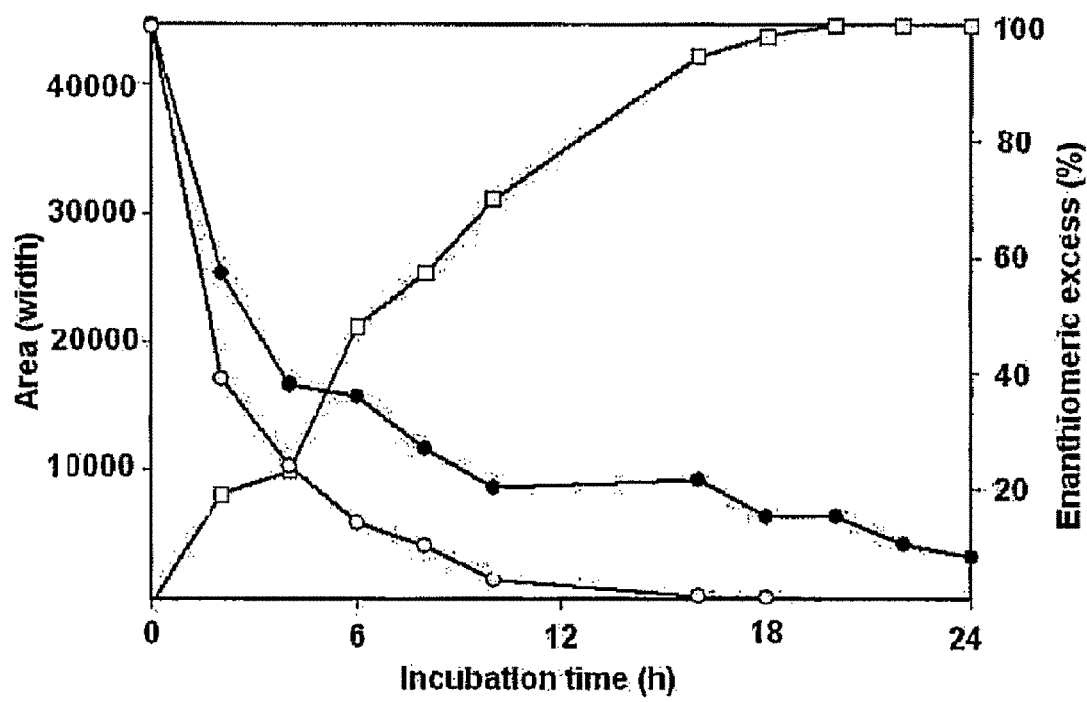
FIG. 2 shows the kinetic resolution of *Erythrobacter* spp. JCS358 toward the racemic SO substrate, wherein ○, ● and □ indicate (R)-styrene oxide area, (S)-styrene oxide area and enantiomeric excess(%), respectively.

As shown in FIG. 2, the kinetic resolution of racemic SO by JCS 358 stain was observed. Wherein, the hydrolyzing rate toward (R)-SO substrate was to be faster than that of (S)-SO substrate, and the enantiopurity of (S)-SO was increased from 0 to 99% after 16 h. However, the fact that it was taken 16 h for kinetic resolution of 2 mM of SO indicates that the endogeneous level of EHase produced by *Erythrobacter* spp. JCS 358 strain was not be enough to efficient kinetic resolution of racemic SO.

EXAMPLE 2

Identification and Phylogenetic Analysis of the EHase Gene from *Erythrobacter Litoralis* HTCC2594 Strain <2-1> Analysis of ORF Sequence from *Erythrobacter Litoralis* HTCC2594 strain To identify EHase gene from *Erythrobacter litoralis* HTCC2594 strain, sequences (Sm-X-Nu-X-Sm-Sm motif and H-G-P) toward ORF sequence of above strain whose genome sequence was known by Moore foundation (Palo Alto, CA.) were analyzed with the ProteinFinder program of Ensoltek (Yuseong-gu, Daejeon, Korea) and the BLAST program. Also, the pair wise comparison of amino acid sequence of candidate EHase and known EHase were analyzed with the CLUSTAL W program (Thompson, et al., Nucleic. Acids. 22: 4673-4680, 1994). It was analyzed with general method whether the active-site residues of putative EHase was presented in the candidate strains. For this purpose, sequences that contained ring-opening tyrosine, HGXP motif and Sm-X-Nu-Sm-Sm(Sm=small residue, X=any residue, and Nu=nucleophile) motif were selected, and aligned with the known EHase sequences.

Figure 3B:
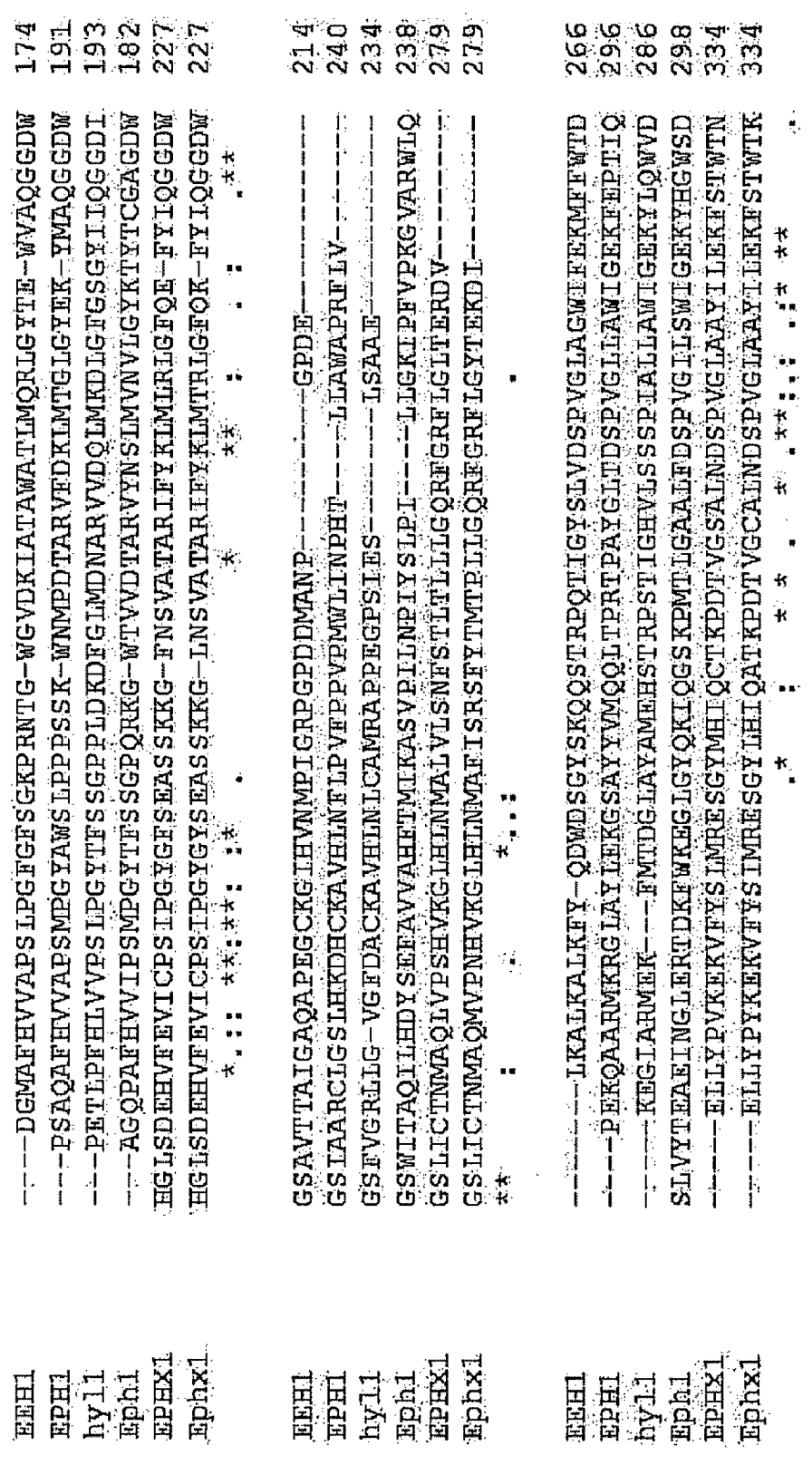

The results indicated that FIG. 3A to 3C were aligned amino acid sequence of purified EEH1 protein with that of known protein, wherein the protein accession numbers were followed as:

EPH1 (*Rhodotorula glutinis*), AAF64646;
Ephx1 (*Rattus norvegivcu*), P07687;
EPHX1 (*Homo sapiens*), AAH08291;
Eph1 (*Xanthophyllomyces dendrorhous*), AAF18956;
hyl1 (*Aspergillus niger*), CAB59813 and
EEH1 (*Erythrobacter litoralis* HTCC2594).

The results indicated that FIGS. 4A and 4B were aligned amino acid sequence of purified EEH2 and EEH3 protein with that of known protein, wherein the protein accession numbers were followed as:

*Homo sapiens* (EPHX2, Human sEH), AAH11628;
*Rattus norvegicus* (Ephx2, Rat sEH), CAA46211;
*Solanum tuberosum* (pEHSt and potato sEH), AAA81890;
*Glycine max* (sEHGm and soybean sEH), CAA55293;
*Bradyrhizobium japonicum* (ephA), BAC46379;
*Erythrobacter litoralis* HTCC2594 (EEH2) and
*Erythrobacter litoralis* HTCC2594 (EEH3).

The results of analyzing the ORF sequence of *Erythrobacter litoralis* HTCC2594, three genes consisting of 1.122 by (eeh1, SEQ ID NO: 14), 870 by (eeh2, SEQ ID NO: 16) and 888 by (eeh3, SEQ ID NO: 18) were selected. Also, it was confirmed that most of EHases contained shared Sm-X-Nu-X-Sm-Sm motif, catalytic triad and oxyanion hole (FIG. 3 and FIG. 4). Firstly, eeh1 gene showed 35% of similarity to human microsomal EHase, and contained GGD$^{173}$WGS motif, catalyst triad (Asp$^{173}$, Glu$^{324}$ and His$^{351}$) and oxyanion hole HGXP (HGW$^{99}$P)(FIG. 3A to 3C). In contrast, eeh2 and eeh3 genes showed similarity to soluble EHase containing Sm-X-Nu-X-Sm-Sm motif (VHD$^{107}$YGV for eeh2 and AHD$^{106}$WGA for eeh3), catalytic triad (Asp$^{107}$, Glu$^{250}$ and His$^{269}$ for eeh2; Asp$^{106}$, Glu$^{251}$ and His$^{270}$ for eeh3) and oxyanion hole HGXP (HGY$^{42}$P for eeh2 and HGF$^{38}$P for eeh3) conserved in EHase (Arahira et al., 2000; Kaneko et al., 2002; Knehr et al., 1993; Stapleton et al., 1994 and Strausberg et al., 2002; FIGS. 4A and 4B).

<2-2> Phylogenetic Analysis

For phylogenetic analysis of EHase, the known EHase sequences received from SwissProt or EMBL protein database were compared with sequences of eeh1, eeh2 and eeh3 gene. Phylogenetic distances were calculated with the CLUSTAL W program and phylogenetic trees were drawn with the Molecular Evolutionary Genetics Analysis 3.1 software (The Biodesign Institute, Tempe, Ariz.; Kumar et al., 2004). The results indicated that FIG. 5 was drawn by phylogenetic analysis of EHase, wherein the protein accession numbers were followed as:

*Rhodotorula glutinis* (AAF64649);
*Rattus norvegicus* (P07687);
*Homo sapiens* (AAH08291);
*Xanthophyllomyces dendrorhous* (AAF18956);
*Aspergillus niger* (CAB59813);
*Homo sapiens* (AAH11628);
*Rattus norvegicus* (CCA46211);
*Solanum tuberosum* (AAA81890);
*Glycine max* (CAA55293);
*Agrobactrium radiobacter* sEEH (O31243);
*Corynebacterium* spp. sEEH (O52866) and
Haloalkane dehalogenase (P22643).

Figure 5:
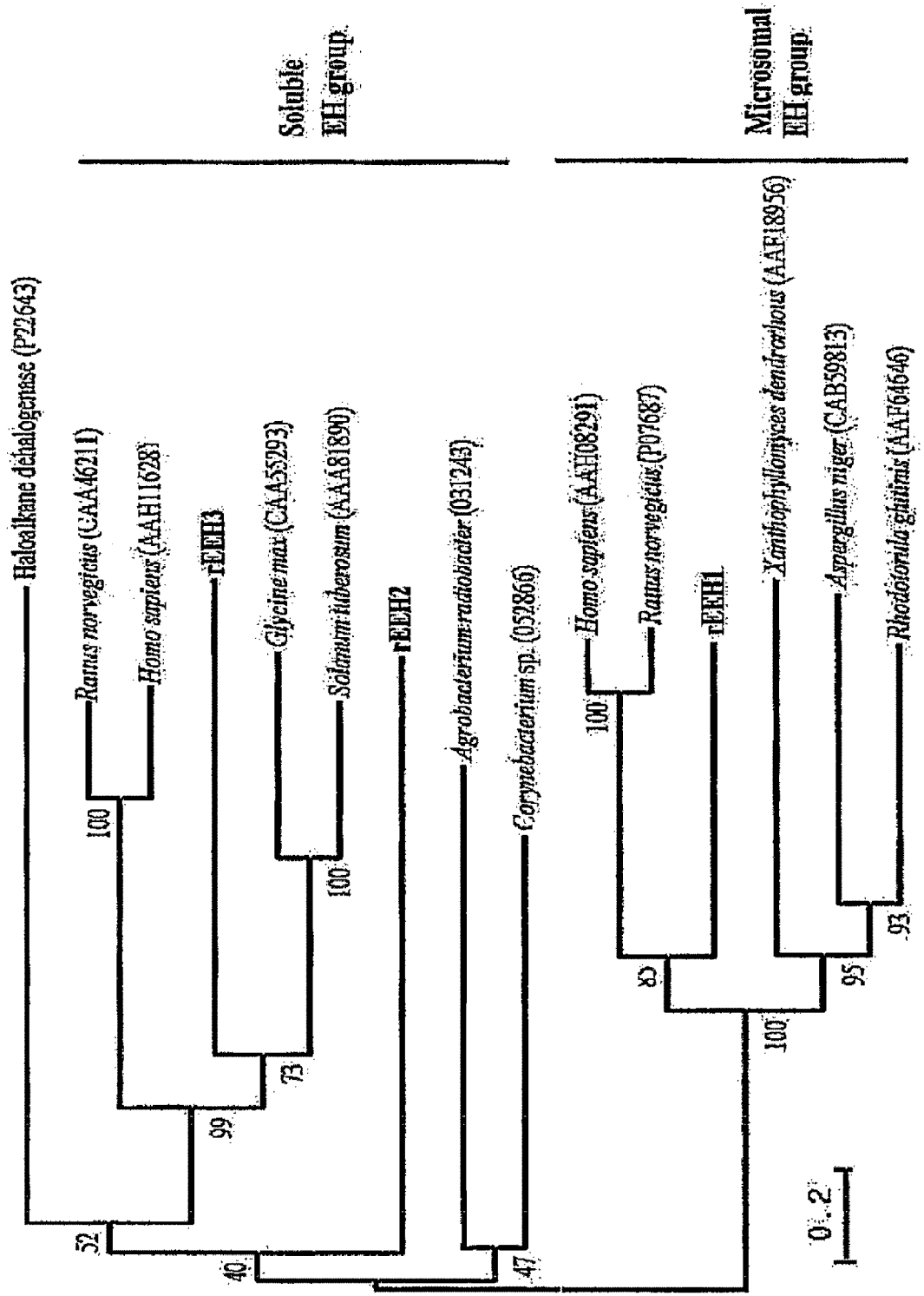
FIG. 5 shows a phylogenetic analysis of epoxide hydrolase (EHase).

As shown in FIG. 5, a phylogenetic analysis of the three ORFs with ORFs of known EHase from *Rhodotorula glutinis* (EPH1; Visser et al., 2000), *Rattus norvegicus* (Ephx1, Rat mEH; Falany et al., 1987), *Homo sapiens* (EPHX1, Human mEH; Strausberg et al., 2002), *Xanthophyllomyces dendrorhous* (Eph1; Visser et al., 1999), *Aspergillus niger* (hyl1; Arand et al., 1999), *Homo sapiens* (EPHX2, Human sEH; Strausberg et al., 2002), *Rattus norvegicus* (Ephx2, Rat sEH; Knehr et al., 1993), *Solanum tuberosum* (pEHSt and potato; sEH; Stapleton et al., 1994), Glycine max (sEHGm and soybean sEH; Arahira et al., 2000), *Agrobacterium radiobacter* sEEH (Rink et al., 1997), *Corynebacterium* spp. sEEH (Misawa et al., 1998), and Haloalkane dehalogenase (Janssen et al., 1989) was conducted using modified neighbor-joining method. The results indicated that eeh1 was related to group with microsomal EHase, while eeh2 and eeh3 were related to soluble EHase (FIG. 5). Taken together, the ORFs of the present invention from *Erythrobacter litoralis* HTCC2594 were EHase having the hydrolyzing activity toward epoxide substrates.

<2-3> Cloning of eeh Genes

To cloning of EHase encoding genes from *Erythrobacter litoralis* HTCC2594 strain, the genomic DNA of above strain was isolated using the Genomic DNA extraction kit (Promega, USA), and was amplified with Forward(F) and Reverse(R) primer set flanked by restriction enzyme Nde I and Xho I/Not I site as indicated in Table 3, respectively.

TABLE 3

Primer set for cloning of eeh genes

| PRIMER | SEQUENCE | SEQ ID NO: |
|---|---|---|
| eeh1F (F) | 5'-CGACCCGGCATATGAGCGAGATCAGGCCCTTCG TTCT-3' | 4 |
| eeh1R (R) | 5'-CTCCACATCTCGAGTCGCATGAGTGAAAAACAG GCGCG-3' | 5 |
| eeh2F (F) | 5'-CGACCCGGCATATGGCCGGACCAAGCCTGGGCG AATGG-3' | 6 |

TABLE 3-continued

Primer set for cloning of eeh genes

| PRIMER | SEQUENCE | SEQ ID NO: |
|---|---|---|
| eeh2R (R) | 5'-CTCCACATCTCGAGGCGTGCGAGCCAATCCAGC GTCACGC-3' | 7 |
| eeh3F (F) | 5'-CGACCCGGCATATGCCCGATCCTGCGAGCGGGA TT-3' | 8 |
| eeh3R (R) | 5'-CTCCACATGCGGCCGCGGATGCCGGAGCGGGCT TAGG-3' | 9 |
| eeh1RX (R) | 5'-CTCCACATCTCGAGCTATCGCATGAGTGAAAAA CAGGC-3' | 10 |
| eeh2RX (R) | 5'-CTCCACATCTCGAGTTAGCGTGCGAGCCAATCC AGCGTCACGC-3' | 11 |
| eeh3RX (R) | 5'-CTCCACATGCGGCCGCTCAGGATGCCGGAGCGG GCTTAG-3' | 12 |

As shown in Table 3, the underlined sequences in the forward and reverse primer indicate Nhe I and Xho I/Not I site, respectively. For confirm the expression of eeh1, eeh2 and eeh3 genes without His-tag, the reverse primers of eeh1RX, eeh2RX and eeh3RX were also designed as above Table 3. After PCR, the amplified DNA fragment was restricted with restriction enzyme Nhe I and Xho I/Not I, and the fragment was ligated with Nhe I and Xho I/Not I-restricted plasmid pET-24a (+) vector, and then the vector was transformed into *E. coli* DH5α. The recombinant vector was introduced into BL21-CondonPlus(DE3)-RP(Novagen) for expression.

<2-4> Expression of eeh Genes

To confirm whether the eeh gene expression vector which was manufactured with the method as described above embodiment <2-3> was expressed in the cells, the transformant was cultured at 37° C., and was induced by the addition of 1 mM IPTG when the optical density(O.D) reached 0.4 to 0.6 at 600 nm. 3 h after induction, the cells were harvested by centrifugation at 5,000×g for 20 min, resuspended in a buffer [50 mM phosphate (pH 7.0), 0.5 M KCl and 10% glycerol], and then disrupted by sonication. Cell debris was removed by centrifugation at 15,000×g for 30 min using a His-Bind Purification Kit (Novagen Co.). The soluble fraction was loaded in a Ni-nitrilotriacetic(Ni-NTA) column equilibrated with binding buffer [500 mM NaCl, 20 mM phosphate (pH 7.0), and 5 mM imidazole]. After washing with washing buffer [500 mM NaCl, 20 mM phosphate (pH 7.0), and 60 mM imidazole], the bound enzyme was eluted with elution buffer [500 mM NaCl, 20 mM phosphate (pH 7.0), and 1 M imidazole], and then dialyzed with 50 mM of phosphate buffer (pH 7.0). The purity of the protein was confirmed by SDS-PAGE under denaturing conditions as described by Laemmli (1970). The protein concentration was measured by the Bradford method using the Bio-Rad protein assay kit containing a standard protein BSA (Bradford, 1976).

Figure 6:
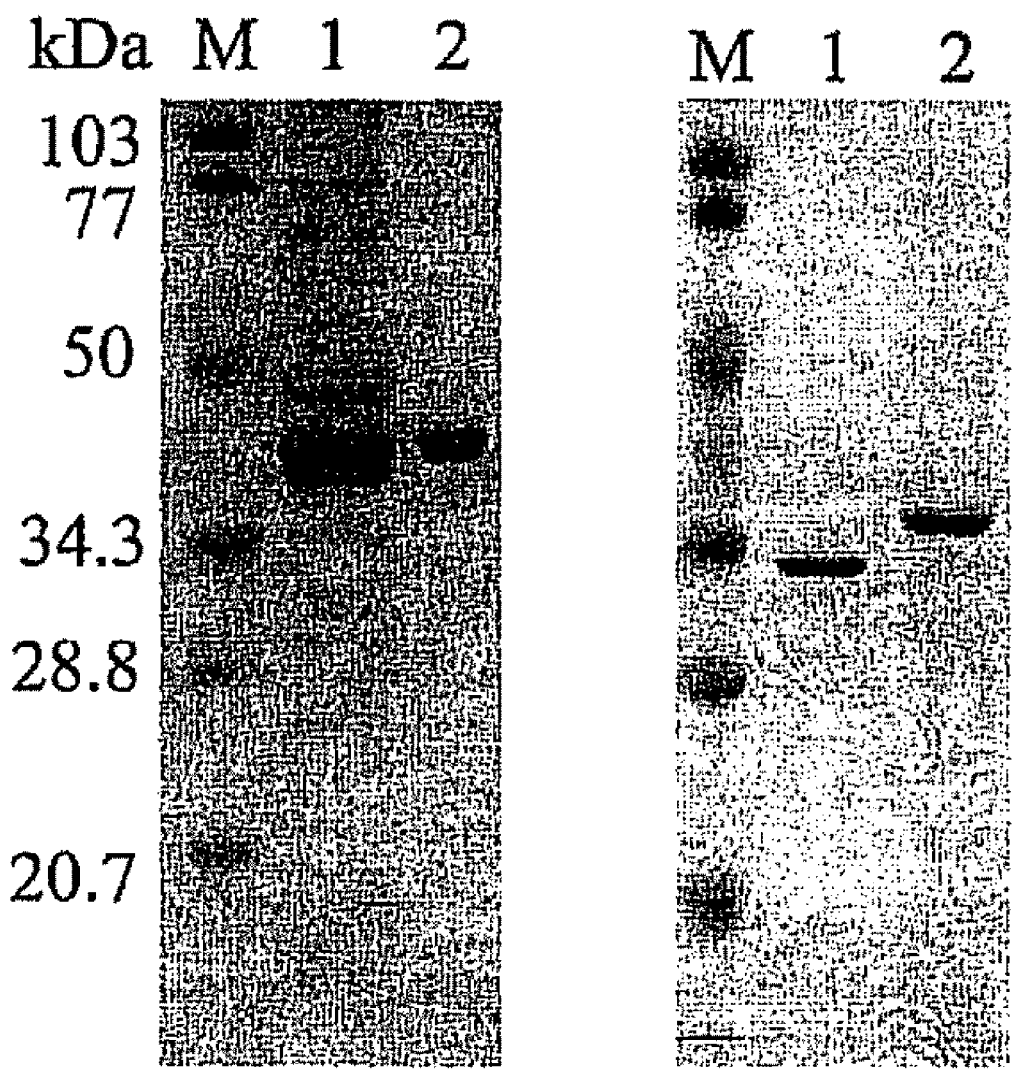
FIG. 6 shows the purity of three EHases isolated from *Erythrobacter litoralis* HTCC2594 with SDS-PAGE, wherein FIG. A indicates purified EEH1, B indicates purified EEH2 and EEH3, respectively.

The results indicated that the molecular weight of the purified rEEH1, rEEH2, and rEEH3 showed 41 kDa (rEEH1, SEQ ID NO: 13), 33.4 kDa (rEEH2, SEQ ID NO: 15), and 34.5 kDa (rEEH3, SEQ ID NO: 17), respectively (FIGS. 6A and 6B).

<2-5> The Effects of pH and Temperature on the EHase Activity

The effect of pH on the EHase activity was measured with 50 mM sodium acetate-acetic acid buffer (pH 4.0 and 6.0), 50 mM MES buffer (pH 6.0 to 7.0), 50 mM Phosphate buffer (pH 7.0 to 9.0), and 50 mM Glycine buffer (pH 9.0 and 10.0), and the optimum reaction temperature on the EHase activity was measured over a temperature of range from 10 to 70° C. at pH 7.5.

Figure 7A:
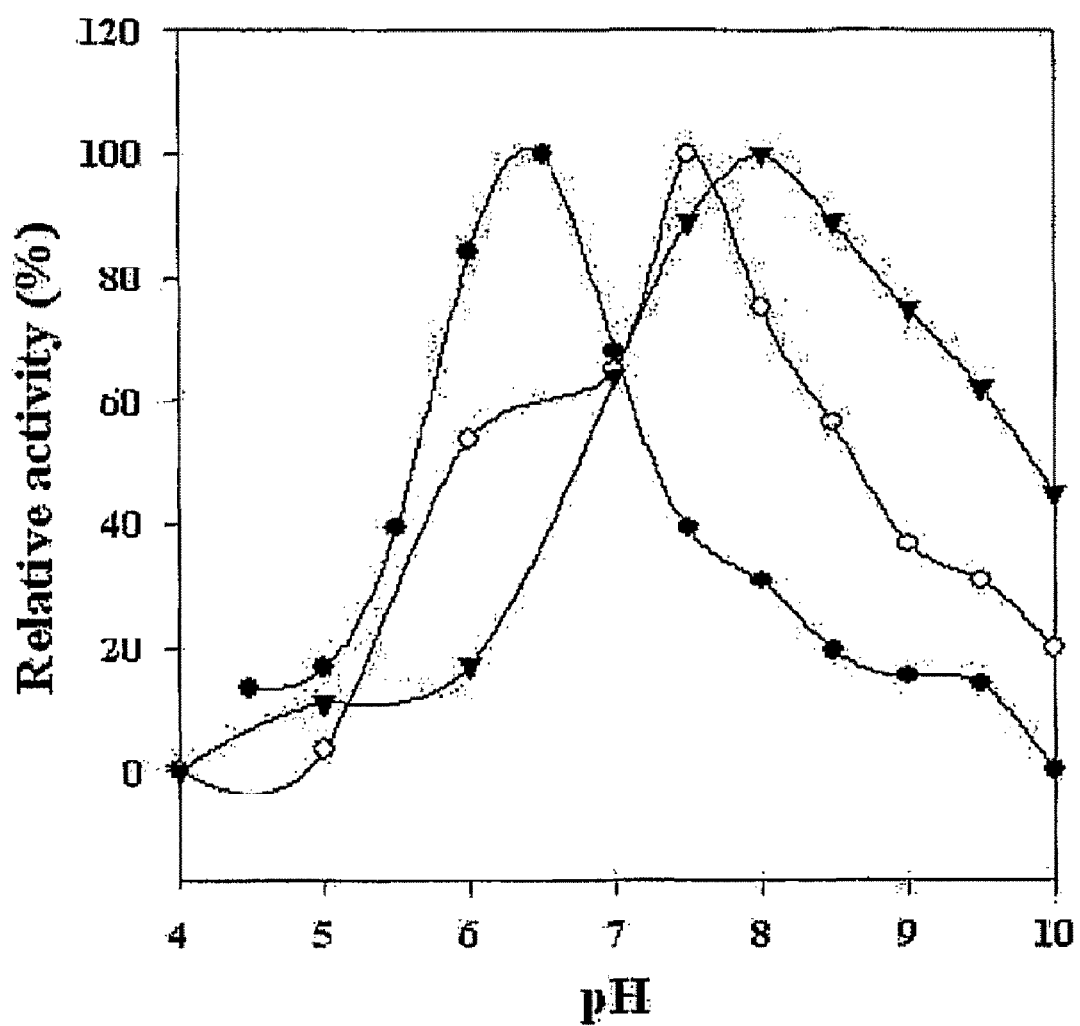
FIGS. 7A and 7B show the effects of pH and temperature on the activity of the purified rEEH1, rEEH2 and rEEH3, wherein ○, ● and ▼ indicate EEH1, EEH2 and EEH3, respectively.

The effect of pH on the activity of the EHases (rEEH1, rEEH2 and rEEH3) was measured with varying pH of range from 4.0 to 10.0, and the results indicated that the optimum activity of the rEEH1, rEEH2 and rEEH3 toward styrene oxide occurred at pH 6.5, 7.5, and 8.0, respectively (FIG. 7A). Namely, the EHases were stable largely at neutral pH, but unstable under pH 6.0 (FIG. 7A).

Figure 7B:
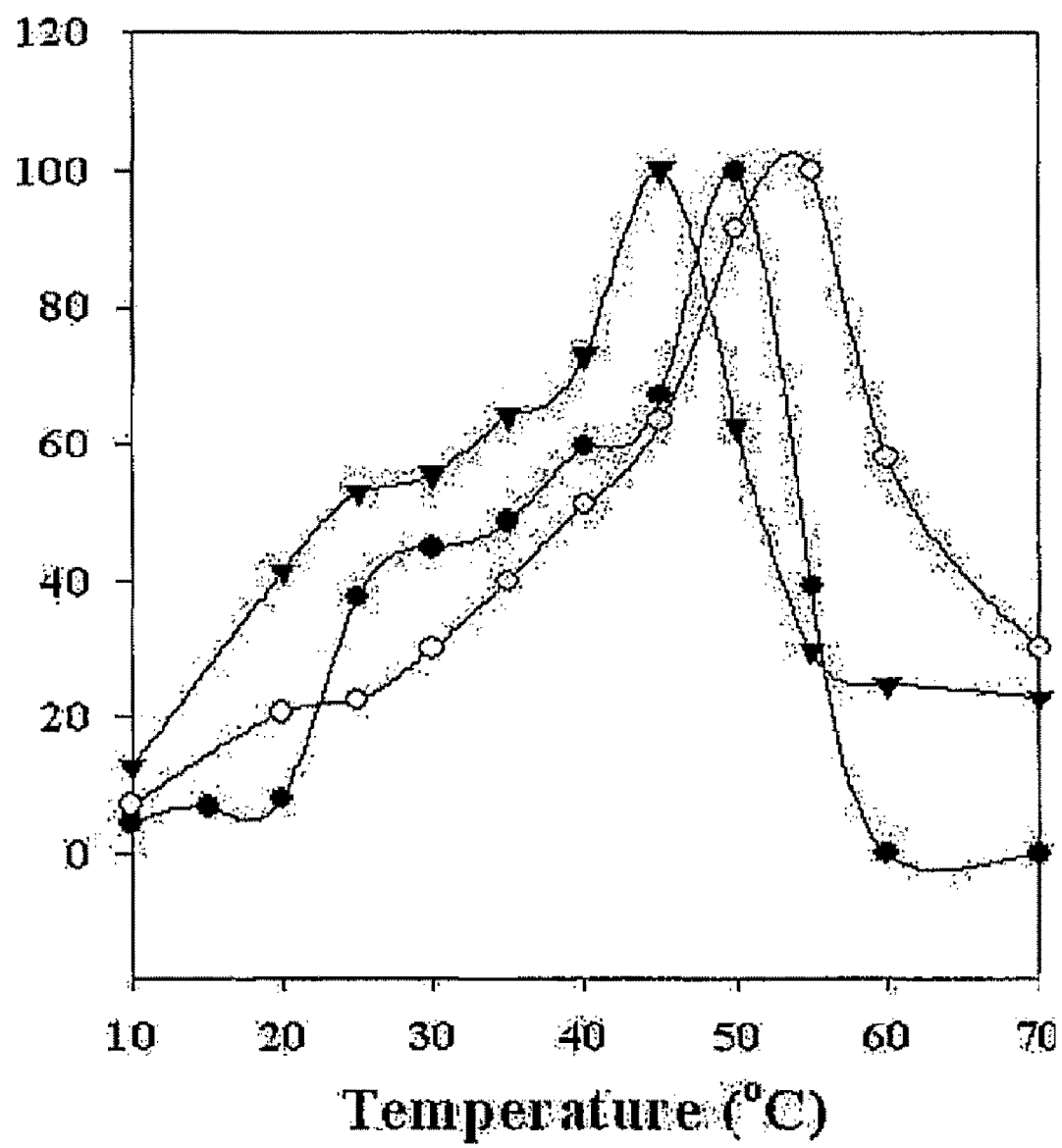

Also, the effect of temperature on the activity of the EHases (rEEH1, rEEH2 and rEEH3) was measured in the range from 10 to 70° C., the results indicated that the hydrolysis rate of the rEEH1, rEEH2 and rEEH3 was maximum at 50° C., 55° C., and 45° C., respectively (FIG. 7B). Namely, the EHase activity toward the temperature was increased from 10 to 50° C., then obviously decreased above the optimum temperature (FIG. 7B).

EXAMPLE 3

Cloning and Expression of the EHase Genes from *Sphingopyxis Alaskensis, Novosphingobium Aromaticivorans*, and *Rhodobacterium* Sp. HTCC2594

After analyzing the ORF sequences from *Sphingopyxis alaskensis, Novosphingobium aromaticivorans*, and *Rhodobacterium* sp. HTCC2594 with the method as described above embodiment 2, each of genes having the activity of the EHase were cloned with Forward(F) and Reverse(R) primer set as indicated in Table 4.

TABLE 4

Primer set for cloning of the EHase genes from each of strains

| PRIMER | SEQUENCE | SEQ ID NO: |
|---|---|---|
| SPF1 (F) | 5'-CGACCCGGCATATGTCCCCCGCCAAATCAATTT CGC-3' | 19 |
| SPRH1 (R) | 5'-CTCCACATGCGGCCGCCTTCTTCTCGCGCAAGG GG-3' | 20 |
| NVF1 (F) | 5'-CGACCCGGCATATGAATGTTGCGCCTTTCGTTG TCG-3' | 21 |
| NVRH1 (R) | 5'-CTCCACATGCGGCCGCGCACATCAGGGAAAACG CGG-3' | 22 |
| RBF2 (F) | 5'-CGACCCGGCATATGAACGACAAGACCTTTATCG AGACGAACGGC-3' | 23 |
| RBRH2 (R) | 5'-CTCCACATCTCGAGTTACAAGGCTGAAAAGAAC ACTCGCAAATC-3' | 24 |
| SPRNH1 (R) | 5'-CTCCACATGCGGCCGCTCACTTCTTCTCGCGCA AGGG-3 | 25 |
| NVRNH1 (R) | 5'-CTCCACATGCGGCCGCCTAGCACATCAGGGAAA ACGCG-3' | 26 |
| BRNH2 (R) | 5'-CTCCACATCTCGAGTCAAAGCGTGGCGAGCCAG TCGATGA-3' | 27 |

See Table 4. For confirm the expression of sEEH, rEEH, and rEEH genes without His-tag, the reverse primers of SPRNH1 (SEQ ID NO: 25), NVRNH1 (SEQ ID NO: 26) and RBRNH2 (SEQ ID NO: 27) were also designed as above Table 4.

The results indicated that the seeh gene (SEQ ID NO: 29) from *Sphingopyxis alaskensis*, the neeh gene (SEQ ID NO: 31) from *Novosphingobium aromaticivorans*, the reeh gene (SEQ ID NO: 33) from *Rhodobacterium* sp. HTCC2594 were isolated, respectively.

After cloning the genes into pET-24a (+) expression vector, the vector was introduced into BL21-CondonPlus(DE3)-RP (Novagen), and then separated by SDS-PAGE. The results indicated that the molecular weight of the purified sEEH, nEEH, and rEEH showed 49 kDa (sEEH, SEQ ID NO: 28), 43 kDa (nEEH, SEQ ID NO: 30), and 36 kDa (rEEH, SEQ ID NO: 39), respectively (FIG. 9). Also, the optimum activities of sEEH, nEEH, and rEEH occurred at neutral pH and mesophilic conditions (30 to 40° C.).

EXAMPLE 4

Determination of Kinetic Parameters and Substrate Selectivity

Kinetic parameters of the rEEH1, rEEH2, rEEH3, sEEH, nEEH, and rEEH were determined by a GC analysis using (R)- or (S)- styrene oxide substrate. 100 ul of purified EHases were mixed with various concentrations of (R)- or (S)- styrene oxide in a 10 ml tube containing 1 ml of potassium phosphate buffer (100 mM, pH 8.0), and shake-incubated at 200 rpm and a temperature of 30° C. The extraction mixtures were extracted with 2 ml of hexane, and enantiomeric excess [ee; ee=100×(S−R)/(S+R)] toward enantiopure styrene oxide was analyzed with a chiraldex gamma-cyclodextrin trifluoroacetyl(G-TA) capillary GC column. See Table 5 and FIG. 8. Wherein, the FIG. 8 was diagramed with GC analysis for the hydrolyzing activities of enantioselective EHases (rEEH1, rEEH2, and rEEH3) toward racemic styrene oxide.

Solid line: SO,
Bold solid line: SO incubated with rEEH1,
Long dashed line: SO incubated with rEEH2,
Dotted line: RSO incubated with rEEH3.

Figure 8:
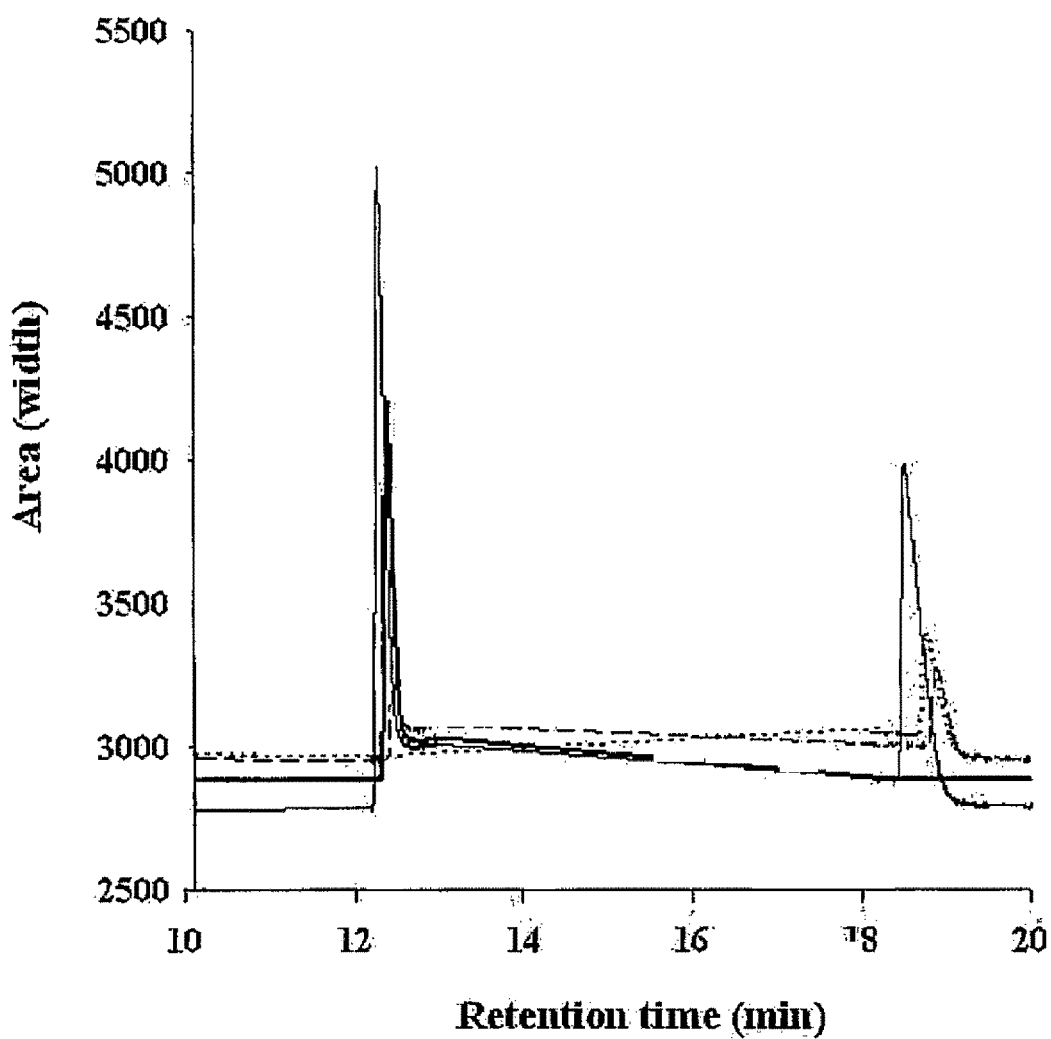
FIG. 8 shows the hydrolyzing activities of enantioselective EHases (EEH1, EEH2 and EEH3) toward the racemic SO substrate with gas chromatography.

The results indicated that $V_{max}^R$ and $K_m^R$ of the purified rEEH1 toward (R)-styrene oxide were 2.3 umol/min and 2.9 mM, respectively, while $V_{max}^S$ and $K_m^S$ of the purified rEEH1 toward (S)-styrene oxide were 1.18 umol/min and 2.3 mM, respectively (Table 5 and FIG. 8). These results revealed that (R)-styrene oxide was hydrolyzed faster than (S)-styrene oxide in rEEH1. Namely, the faster hydrolyzing rate toward an enantiomer implied that the rEEH 1 was enantioselective. In contrast, $V_{max}^S$ and $K_m^S$ of the purified rEEH3 toward (S)-styrene oxide were 0.43 umol/min and 3.71 mM, respectively, while $V_{max}^R$ and $K_m^R$ of the purified rEEH3 toward (R)-styrene oxide were 0.29 umol/min and 2.61 mM, respectively (Table 5 and FIG. 8). These results revealed that (S)-styrene oxide was hydrolyzed faster than (R)-styrene oxide in rEEH3. On the other hand, $V_{max}^S$ and $K_m^S$ of the purified rEEH2 toward (S)-styrene oxide were 0.12 umol/min and 6.18 mM, respectively, while $V_{max}^R$ and $K_m^R$ of the purified rEEH2 toward (R)-styrene oxide were 0.11 umol/min and 5.49 mM, respectively (Table 5 and FIG. 8). These results revealed that both of (S)-styrene oxide and (R)-styrene oxide were hydrolyzed at an equal rate in rEEH2.

In the catalytic efficiency ($k_{cat}/K_m$) of rEEH1, rEEH2 and rEEH3, the hydrolyzing activity of rEEH1 was appeared to approximately 60 to 550 fold higher than rEEH2 and rEEH3 (Table 5). These results indicated that the enantioselective activity of whole cells was resulted from the dominant activity of rEEH1.

TABLE 5

Kinetic parameters of the rEEH1, rEEH2 and rEEH3 toward the hyrolysis of (R)- and (S)-styrene oxide

| Enzyme | Km mM | Vmax μmole/min | kcat s$^{-1}$ | kcat Km s$^{-1}$ mM$^{-1}$ |
|---|---|---|---|---|
| (S)-enantiomer | | | | |
| rEEH1 | 2.3 | 1.1 | 24.5 | 10.6 |
| rEEH2 | 6.1 | 0.1 | 1.7 | 0.2 |
| rEEH3 | 3.7 | 0.4 | 6.5 | 1.7 |
| (R)-enantiomer | | | | |
| rEEH1 | 2.9 | 2.3 | 49.1 | 16.3 |
| rEEH2 | 5.4 | 0.1 | 1.6 | 0.3 |
| rEEH3 | 2.6 | 0.2 | 4.3 | 1.6 |

Also, the substrate selectivity of rEEH1, rEEH2 and rEEH3 toward various epoxide substrates depicted in FIG. 1 was same to Table 4. The results indicated that the purified rEEH1 hydrolyzed enantioselectively toward monosubstituted epoxides with bulky ring at C-1 position, whereas hydrolyzed both of (R)- and (S)-monosubstituted epoxides with aliphatic chains at similar rate. In contrast, the purified rEEH3 hydrolyzed enantioselectively aliphatic epoxides at C-1 position and styrene oxide, but the enantioselective differentiation was not found.

TABLE 6

Enantioselective hydrolyzing activity of the rEEH1, rEEH2 and rEEH3 toward various epoxide substrates

| | Hydrolysis rate (×10$^{-2}$) mg/min | | | | | | | | | | | |
|---|---|---|---|---|---|---|---|---|---|---|---|---|
| | SO | | GPE | | EX | | EB | | ECH | | EF | |
| Enzyme | (S) | (R) | (S) | (R) | (S) | (R) | (S) | (R) | (S) | (R) | (S) | (R) |
| rEEH1 | 9.00 | 28.0 | 20.0 | 11.0 | 8.00 | 7.00 | 15.0 | 15.0 | N.D. | N.D. | 15.0 | 4.00 |
| rEEH2 | 0.06 | 0.05 | 0.07 | 0.06 | 0.07 | 0.07 | 0.08 | 0.08 | 0.23 | 0.23 | N.D. | N.D. |
| rEEH3 | 0.14 | 0.10 | 0.10 | 0.10 | 0.09 | 0.17 | 0.11 | 0.08 | 0.28 | 0.26 | N.D. | N.D. |

* N.D: not determined

Kinetic parameters were estimated by non-linear regression analysis using a Sigma Plot program, and various substrates as depicted in FIG. 1 were also tested for the enantioselective hydrolyzing activity by rEEH1, rEEH2, rEEH3, sEEH, nEEH, and rEEH. See Table 6. The results indicated that the rEEH hydrolyzed (R)-enantiopure styrene oxide, while nEEH and sEEH were not enantioselective.

TABLE 7

Kinetic parameters of the enzyme purified from each strains toward (R)- and (S)-styrene oxide

| Enzyme and enantiomer | Parameter value | | | |
|---|---|---|---|---|
| | $K_m$ (mM) | $V_{max}$ (umole/min/mg) | $K_{cat}$ (S-1) | $K_{cat}/K_m$ (S-1/mM) |
| (S)-enantiomer | | | | |
| Sp[a] | 5.25 ± 0.3 | 12.1 | 10.08 | 1.92 |
| Novo[b] | 4 ± 0.3 | 18.67 | 12.96 | 3.24 |
| RH[c] | 4.1 ± 0.3 | 11.26 | 6.7 | 1.63 |

TABLE 7-continued

Kinetic parameters of the enzyme purified from each strains toward (R)- and (S)-styrene oxide

| Enzyme and enantiomer | Parameter value | | | |
|---|---|---|---|---|
| | $K_m$ (mM) | $V_{max}$ (umole/min/mg) | $K_{cat}$ (S-1) | $K_{cat}/K_m$ (S-1/mM) |
| (R)-enantiomer | | | | |
| Sp[a] | 4 ± 0.3 | 8.9 | 7.42 | 1.86 |
| Novo[b] | 6 ± 0.3 | 40.0 | 27.8 | 4.63 |
| RH[c] | 5.2 ± 0.3 | 54.08 | 32 | 6.16 |

[a], [b], and [c]: Enzyme purified from *Sphingopyxis alaskensis*, *Novosphingobium aromaticivorans*, and *Rhodobacterium* sp. HTCC2654, respectively.

Therefore, the EHases purified from *Erythrobacter*, *Sphingopyxis*, *Novosphingobium*, and *Rhodobacterium* strains can be applied to bioprocess for production of enantiopure epoxides in the pharmaceutical industry.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method of preparing an enantiopure styrene oxide or glycidyl phenyl ether by reacting a protein having the amino acid of SEQ ID NO: 32 with at least one substrate selected from the group consisting of styrene oxide and glycidyl phenyl ether, to enantioselectively hydrolyze the substrate.

2. The method according to claim 1, wherein the protein is encoded by the nucleotide sequence of SEQ ID NO: 33.

3. The method according to claim 1, wherein the protein has an optimum pH 7.0 to 8.0 and an optimum temperature of 30 to 40° C.

4. An isolated enantioselective epoxide hydrolase protein having the amino acid sequence of SEQ ID NO: 32.

* * * * *

SEQUENCE LISTING

```
<160> NUMBER OF SEQ ID NOS: 43

<210> SEQ ID NO 1
<211> LENGTH: 1450
<212> TYPE: DNA
<213> ORGANISM: Erythrobacter JCS358

<400> SEQUENCE: 1
tggctcagaa cgaacgctgg cggcatgcct acacatgcaa gtcgaacgaa cccttcgggg      60
ttagtggcgc acgggtgcgt aacgcgtggg aacctgccct taggttcgga ataactcaga     120
gaaatttgag ctaataccgg ataatgtctt cggaccaaag atttatcgcc tttggatggg     180
cccgcgtagg attaggtagt tggtggggta aaggcctacc aagccgacga tccttagctg     240
gtctgagagg atgatcagcc acactgggac tgagacacgg cccagactcc tacgggaggc     300
agcagtgggg aatattggac aatgggcgaa agcctgatcc agcaatgccg cgtgagtgat     360
gaaggcctta gggttgtaaa gctctttac cagggatgat aatgacagta cctggagaat     420
aagctccggc taactccgtg ccagcagccg cggtaatacg gagggagcta gcgttgttcg     480
gaattactgg gcgtaaagcg cgcgtaggcg gctcatcaag tcagggtga atcccgggg      540 ctcaaccccg gaactgccct tgaaactggt aggctagaat cctggagagg cgagtggaat     600
tccgagtgta gaggtgaaat tcgtagatat tcggaagaac accagtggcg aaggcgactc     660
gctggacagg tattgacgct gaggtgcgaa agcgtgggga gcaaacagga ttagataccc     720
tggtagtcca cgccgtaaac gatgataact agctgtccgg gttcacagaa cttgggtggc     780
gcagctaacg cattaagtta tccgcctggg gagtacggtc gcaagattaa aactcaaagg     840
aattgacggg ggcctgcaca agcggtggag catgtggttt aattcgaagc aacgcgcaga     900
accttaccag ccttttgacat cctaggacgg tttctggaga cagactcctt cccttcgggg     960
acctagtgac aggtgctgca tggctgtcgt cagctcgtgt cgtgagatgt tgggttaagt    1020
cccgcaacga gcgcaaccct cgtccttagt tgccatcatt tagttgggca ctttaaggaa    1080
actgccggtg ataagccgga ggaaggtggg gatgacgtca agtcctcatg gcccttacag    1140
```

```
gctgggctac acacgtgcta caatggcatc tacagtgagc agcgatcccg cgagggttag    1200
ctaatctcca aaagatgtct cagttcggat tgttctctgc aactcgagag catgaaggcg    1260
gaatcgctag taatcgcgga tcagcatgcc gcggtgaata cgttcccagg ccttgtacac    1320
accgcccgtc acaccatggg agttggattc acccgaaggc ggtgcgctaa ccttttagga    1380
ggcagccgac cacggtgggt tcagcgactg gggtgaagtc gtaacaaggt agccgtaggg    1440
gaacctgcgg                                                           1450
```

<210> SEQ ID NO 2
<211> LENGTH: 20
<212> TYPE: DNA
<213> ORGANISM: Artificial Sequence
<220> FEATURE:
<223> OTHER INFORMATION: Forward primer for 16S rRNA of JCS358(27F)

<400> SEQUENCE: 2

```
agagtttgat catggctcag                                                  20
```

<210> SEQ ID NO 3
<211> LENGTH: 20
<212> TYPE: DNA
<213> ORGANISM: Artificial Sequence
<220> FEATURE:
<223> OTHER INFORMATION: Reverse primer for 16S rRNA of JCS358(1518R)

<400> SEQUENCE: 3

```
aaggaggtga tccagccgca                                                  20
```

<210> SEQ ID NO 4
<211> LENGTH: 37
<212> TYPE: DNA
<213> ORGANISM: Artificial Sequence
<220> FEATURE:
<223> OTHER INFORMATION: Forward primer for EEH1 gene

<400> SEQUENCE: 4

```
cgacccggca tatgagcgag atcaggccct tcgttct                               37
```

<210> SEQ ID NO 5
<211> LENGTH: 38
<212> TYPE: DNA
<213> ORGANISM: Artificial Sequence
<220> FEATURE:
<223> OTHER INFORMATION: Reverse primer for EEH1 gene

<400> SEQUENCE: 5

```
ctccacatct cgagtcgcat gagtgaaaaa caggcgcg                              38
```

<210> SEQ ID NO 6
<211> LENGTH: 38
<212> TYPE: DNA
<213> ORGANISM: Artificial Sequence
<220> FEATURE:
<223> OTHER INFORMATION: Forward primer for EEH2 gene

<400> SEQUENCE: 6

```
cgacccggca tatggccgga ccaagcctgg gcgaatgg                              38
```

<210> SEQ ID NO 7
<211> LENGTH: 40
<212> TYPE: DNA
<213> ORGANISM: Artificial Sequence
<220> FEATURE:
<223> OTHER INFORMATION: Reverse primer for EEH2 gene

```
<400> SEQUENCE: 7
ctccacatct cgaggcgtgc gagccaatcc agcgtcacgc                    40

<210> SEQ ID NO 8
<211> LENGTH: 35
<212> TYPE: DNA
<213> ORGANISM: Artificial Sequence
<220> FEATURE:
<223> OTHER INFORMATION: Forward primer for EEH3 gene

<400> SEQUENCE: 8
cgacccggca tatgcccgat cctgcgagcg ggatt                         35

<210> SEQ ID NO 9
<211> LENGTH: 37
<212> TYPE: DNA
<213> ORGANISM: Artificial Sequence
<220> FEATURE:
<223> OTHER INFORMATION: Reverse primer for EEH3 gene

<400> SEQUENCE: 9
ctccacatgc ggccgcggat gccggagcgg gcttagg                       37

<210> SEQ ID NO 10
<211> LENGTH: 38
<212> TYPE: DNA
<213> ORGANISM: Artificial Sequence
<220> FEATURE:
<223> OTHER INFORMATION: Reverse primer for EEH1 without His-tag

<400> SEQUENCE: 10
ctccacatct cgagctatcg catgagtgaa aaacaggc                      38

<210> SEQ ID NO 11
<211> LENGTH: 43
<212> TYPE: DNA
<213> ORGANISM: Artificial Sequence
<220> FEATURE:
<223> OTHER INFORMATION: Reverse primer for EEH2 without His-tag

<400> SEQUENCE: 11
ctccacatct cgagttagcg tgcgagccaa tccagcgtca cgc                43

<210> SEQ ID NO 12
<211> LENGTH: 39
<212> TYPE: DNA
<213> ORGANISM: Artificial Sequence
<220> FEATURE:
<223> OTHER INFORMATION: Reverse primer for EEH3 without His-tag

<400> SEQUENCE: 12
ctccacatgc ggccgctcag gatgccggag cgggcttag                     39

<210> SEQ ID NO 13
<211> LENGTH: 373
<212> TYPE: PRT
<213> ORGANISM: Erythrobacter litoralis

<400> SEQUENCE: 13

Met Ser Glu Ile Arg Pro Phe Val Leu Asp Val Pro Lys Ala Asp Leu
1               5                   10                  15

Asp Arg Leu His Arg Lys Leu Asp Asp Thr Arg Trp Pro Glu Lys Glu
            20                  25                  30

Pro Val Asp Asp Trp Ser Gln Gly Thr Pro Leu Ala Ala Leu Gln Asp
```

```
                    35                  40                  45
Leu Ala Ala Tyr Trp Arg Asp Gly Tyr Asp Trp Arg Ala Gly Glu Ala
 50                  55                  60

Lys Leu Asn Ala Leu Gly Gln Phe Ile Thr Glu Ile Asp Gly Leu Asp
 65                  70                  75                  80

Ile His Phe Leu His Val Arg Ser Lys Cys Asp Asp Ala Leu Pro Leu
                     85                  90                  95

Ile Leu Thr His Gly Trp Pro Gly Ser Val Arg Glu Phe Phe Asp Val
                100                 105                 110

Ile Pro Leu Leu Thr Glu Pro Gln Asp Gly Met Ala Phe His Val Val
            115                 120                 125

Ala Pro Ser Leu Pro Gly Phe Gly Phe Ser Gly Lys Pro Arg Asn Thr
130                 135                 140

Gly Trp Gly Val Asp Lys Ile Ala Thr Ala Trp Ala Thr Leu Met Gln
145                 150                 155                 160

Arg Leu Gly Tyr Thr Glu Trp Val Ala Gln Gly Asp Trp Gly Ser
                165                 170                 175

Ala Val Thr Thr Ala Ile Gly Ala Gln Ala Pro Glu Gly Cys Lys Gly
                180                 185                 190

Ile His Val Asn Met Pro Ile Gly Arg Pro Gly Pro Asp Asp Met Ala
            195                 200                 205

Asn Pro Gly Pro Asp Glu Leu Lys Ala Leu Lys Ala Leu Lys Phe Tyr
210                 215                 220

Gln Asp Trp Asp Ser Gly Tyr Ser Lys Gln Gln Ser Thr Arg Pro Gln
225                 230                 235                 240

Thr Ile Gly Tyr Ser Leu Val Asp Ser Pro Val Gly Leu Ala Gly Trp
                245                 250                 255

Ile Phe Glu Lys Met Phe Phe Trp Thr Asp Asn Gly Gly Ser Pro Phe
                260                 265                 270

Asp Thr Leu Ser Met Asp Ala Ile Leu Asp Asn Ile Met Leu Tyr Trp
            275                 280                 285

Leu Pro Glu Thr Gly Ala Ser Ala Ala Arg Leu Tyr Trp Glu Ser Phe
290                 295                 300

Ala Arg Phe Gly Glu Gly Thr Val Ala Ile Pro Ala Gly Val Ser Ala
305                 310                 315                 320

Phe Pro Lys Glu Ile Ile Pro Ala Pro Arg Lys Trp Ala Glu Arg Arg
                325                 330                 335

Tyr Ala Asp Leu Val Tyr Trp Asn Glu Cys Glu Lys Gly Gly His Phe
            340                 345                 350

Ala Ala Trp Glu Gln Pro Glu Leu Phe Ala Ala Glu Leu Arg Ala Cys
        355                 360                 365

Phe Ser Leu Met Arg
    370

<210> SEQ ID NO 14
<211> LENGTH: 1122
<212> TYPE: DNA
<213> ORGANISM: Erythrobacter litoralis

<400> SEQUENCE: 14
atgagcgaga tcaggcccct cgttctcgac gttcccaagg ctgatctgga tcggctgcat         60
cgcaagctcg acgatacgcg ctggccggag aaggagccgg tcgacgactg gtcgcaagga        120
acaccgctcg ctgcactgca ggatctcgcc gcctattggc gcgacggcta cgactggcgc        180
gccggcgaag cgaagctcaa tgcgttgggc cagtttatca cggagatcga cggcctcgat        240
```

```
atccatttcc tgcatgtccg gtcgaagtgc gacgatgcac tgccgctgat cctgacccat    300
ggctggcccg gctcggtgcg cgaattcttc gacgtcatcc cgctgctgac cgagccgcag    360
gacggaatgg ctttccatgt cgtcgctccg tcgctgccgg gtttcgggtt ttccggcaag    420
ccgaggaaca caggctgggg cgtcgacaag atcgccacgg catgggccac gctgatgcag    480
cggctcggct acaccgagtg ggtcgcgcaa ggggcgatt ggggctccgc cgtgacgacc     540
gccatcggcg cgcaagcacc tgagggttgc aagggcatcc acgtcaacat gccgatcgga    600
cgaccggggc cggacgacat ggccaatccg ggaccgacg agctcaaggc gttgaaagcg     660
ctcaagttct accaggactg ggactcggga tattccaagc aacagagcac ccgcccgcag    720
acgatcggat acagcctcgt cgattccccg gtgggtctcg ctgggtggat tttcgagaag    780
atgttcttct ggaccgacaa cggcggctcg cccttcgaca cgttgagcat ggacgcgatc    840
ctcgacaaca tcatgcttta ctggctcccc gagaccggag cctcggcggc gcggctttat    900
tgggagagct tcgccaggtt cggcgagggg acggtggcga tacccgccgg ggtgagcgcc    960
tttccgaaag aaatcatccc cgcgccccgc aagtgggcgg agcgtcgcta cgccgacctc   1020
gtctactgga atgaatgcga aagggcgga cacttcgccg cgtgggagca gccggagctg    1080
ttcgccgccg agttgcgcgc ctgttttttca ctcatgcgat ag                      1122
```

<210> SEQ ID NO 15
<211> LENGTH: 289
<212> TYPE: PRT
<213> ORGANISM: Erythrobacter litoralis

<400> SEQUENCE: 15

Met Ala Gly Pro Ser Leu Gly Glu Trp Lys Ala Lys Ala Gln His Phe
1               5                   10                  15

Ala Tyr Asp Gly Leu Gln Ile Ala Phe Trp Thr Gly Gly Lys Pro Asp
            20                  25                  30

Ala Arg Pro Leu Leu Val His Gly Tyr Pro Thr Ala Ser Trp Asp
        35                  40                  45

Trp His Arg Val Trp Glu Thr Leu Gly Ser Lys Tyr His Leu Val Ala
    50                  55                  60

Pro Asp Met Ile Gly Phe Gly Leu Ser Asp Lys Pro Arg Ser Gly Tyr
65                  70                  75                  80

Ser Ile His Arg Gln Ala Asp Met His Val Ala Leu Leu Asp His Leu
                85                  90                  95

Gly Ile Gly Ala Phe Asp Ala Leu Val His Asp Tyr Gly Val Ser Val
            100                 105                 110

Gly Gln Glu Leu Leu Ala Arg Arg Ala Glu Arg Ser Ala Ala Gln Gly
        115                 120                 125

Leu Gly Gln Thr Val Phe Leu Asn Gly Gly Ile Phe Pro Asp Gln His
    130                 135                 140

Arg Pro Arg Pro Ile Gln Lys Leu Gly Thr Ser Pro Leu Gly Phe Leu
145                 150                 155                 160

Val Gly Leu Leu Thr Asn Arg Glu Lys Phe Gly Arg Ser Phe Ser Glu
                165                 170                 175

Val Phe Gly Pro Asp Thr Gln Pro Gly Ala Gln Glu Leu Asp Glu Phe
            180                 185                 190

Trp Asp Leu Val Ser His Asn Gly Gly Asn Arg Ile Met His Lys Leu
        195                 200                 205

Leu His Tyr Ile Ala Asp Arg Lys Glu His Ala Glu Arg Trp Phe Asp
    210                 215                 220

```
Ala Leu Arg Ile Ala Gln Gly Asp Ile Gly Leu Ile Asn Gly Ala Leu
225                 230                 235                 240

Asp Pro Val Ser Gly Arg His Ala Tyr Glu Ala Trp Arg Glu Arg Leu
            245                 250                 255

Pro Asp Ala Arg His His Leu Ile Pro Thr Val Gly His Tyr Pro Gln
        260                 265                 270

Val Glu Asp Pro Gln Thr Val Ser Arg Val Thr Leu Asp Trp Leu Ala
    275                 280                 285

Arg
```

<210> SEQ ID NO 16
<211> LENGTH: 870
<212> TYPE: DNA
<213> ORGANISM: Erythrobacter litoralis

<400> SEQUENCE: 16

```
atggccggac caagcctggg cgaatggaag gccaaggcgc agcacttcgc ctacgacggt    60
ctgcaaatcg ccttctggac cggcggcaag ccggatgcac ggccgctgct gctggtgcac   120
ggctatccga cggcctcgtg ggactggcac cgggtctggg agacgctcgg cagcaaatac   180
catctcgttg cgcccgacat gatcggcttc ggcctctcgg acaagccgcg ctcgggctat   240
tcgatccatc gccaggccga catgcatgtg cgctgctcg atcatctggg catcggcgcg   300
ttcgatgcgc tggtgcacga ttacggcgtt ccgttgggc aggaactgct cgcccgtcgg   360
gccgagagat cggcggcgca ggggctcggc caaacagtct tcctcaacgg cggtatcttt   420
cccgaccagc accgcccgcg cccgatccag aagctcggca cgtcgccgct cggcttcctc   480
gtcggcctgc ttaccaaccg tgagaaattc ggcaggagct tttccgaggt cttcggcccg   540
gacacccagc ccggcgcgca ggagctggac gaattctggg acctcgtcag ccacaacggc   600
ggcaaccgca tcatgcacaa gctgctgcac tatatcgccg accgcaaaga gcatgccgaa   660
aggtggttcg acgcactcag gatcgcgcaa ggcgatatcg gcctcatcaa tggcgcgctc   720
gacccggtct ctggccggca tgcctacgaa gcctggcgcg agcggctgcc cgacgcgcgg   780
catcacctga tcccgaccgt gggccattat ccgcaggtgg aggacccgca gacggtgtcg   840
cgcgtgacgc tggattggct cgcacgctaa                                    870
```

<210> SEQ ID NO 17
<211> LENGTH: 295
<212> TYPE: PRT
<213> ORGANISM: Erythrobacter litoralis

<400> SEQUENCE: 17

```
Met Pro Asp Pro Ala Ser Gly Ile Ala Ile Asn Arg Val Pro Ala Asn
1               5                   10                  15

Gly Leu Glu Phe Glu Val Ala Met Ala Gly Glu Gly Asp His Leu Ala
            20                  25                  30

Leu Met Leu His Gly Phe Pro Glu Leu His Phe Ser Trp Arg His Gln
        35                  40                  45

Met Pro Leu Leu Ala Glu Met Gly Tyr Arg Val Trp Ala Pro Asn Met
    50                  55                  60

Arg Gly Tyr Gly Glu Thr Thr Arg Pro Thr Glu Val Arg Asp Tyr Ala
65                  70                  75                  80

Leu Asp His Leu Thr Gln Asp Val Ala Ala Leu Ile Asp Ala Ser Gly
                85                  90                  95

Ala Thr Lys Val Thr Leu Ile Ala His Asp Trp Gly Ala Ile Ile Ala
```

```
                  100                 105                 110
Trp Tyr Phe Ala Ile Leu Lys Leu Arg Pro Leu Glu Arg Leu Val Ile
        115                 120                 125

Met Asn Val Pro His Pro Lys Val Leu Gln Arg Glu Leu Arg Arg Trp
130                 135                 140

Glu Gln Ile Lys Lys Ser Trp Tyr Val Phe Phe Gln Leu Pro Trp
145                 150                 155                 160

Leu Pro Glu Lys Arg Ile Gly Ala Asp Ser Gly Lys Arg Ile Gly Glu
                165                 170                 175

Leu Phe Ala Gln Thr Ser Cys Asn Pro Glu Arg Phe Gly Pro Asp Val
        180                 185                 190

Lys Ala Val Tyr Ala Ala Gly Ala Ala Arg Pro Gly Ala Pro Arg Ala
                195                 200                 205

Met Val Asn Tyr Tyr Arg Ala Ala Met Arg His Arg Asp Thr Ile Asp
210                 215                 220

Pro Gly Asp Phe Arg Val Asp Val Pro Thr Leu Leu Val Trp Gly Glu
225                 230                 235                 240

Glu Asp Val Ala Leu Asn Ile Arg Cys Thr Glu Gly Thr Glu Gln Trp
                245                 250                 255

Val Pro Asp Ile Thr Val Lys Arg Leu Pro Asn Val Ser His Trp Val
                260                 265                 270

Gln Gln Asp Ala Pro Asp Glu Val Asn Ala Ile Leu Arg Glu Trp Leu
        275                 280                 285

Pro Lys Pro Ala Pro Ala Ser
        290                 295

<210> SEQ ID NO 18
<211> LENGTH: 888
<212> TYPE: DNA
<213> ORGANISM: Erythrobacter litoralis

<400> SEQUENCE: 18
atgcccgatc ctgcgagcgg gattgcgatc aatcgggtcc ccgccaatgg cttggaattc      60
gaagtcgcga tggcgggtga gggcgatcac ctcgcgctca tgctgcacgg cttttcccgag    120 ctgcatttca gctggcgtca ccaaatgccg ctattggcag aaatgggcta ccgcgtctgg     180
gcgcccaata tgcgcggtta tggcgagacg acgcgtccaa cggaagtgcg cgactatgcg     240
ctcgatcacc tgacgcagga tgttgcggcg ctgatcgatg cgagcggggc gacaaaagtg     300
acgctgatcg cgcatgactg gggcgcgatc atcgcgtggt atttcgccat cctgaaactg     360
cgaccgctcg agcggctggt gatcatgaat gtgccgcacc ccaaggttct tcagcgcgag     420
ttgcggcggt gggagcagat caagaagagt tggtatgtgt tcttctttca acttccgtgg     480
ctgccggaaa agcgcatcgg tgcggacagc ggcaagcgga tcggcgagct attcgcgcag     540
acgagctgca atccggagcg gttcgggccg gatgtgaagg cggtctatgc tgccggtgcc     600
gcgaggccgg gcgcgccgcg agcgatggtg aattattatc gcgcggcgat gcggcaccgc     660
gacacgatcg atccgggcga tttccgcgtc gatgttccaa cgctattggt ttggggcgag     720
gaggacgttg cgctcaatat ccgttgcacc gaaggcaccg agcaatgggt gcccgatatc     780
acggtcaaac gcctgcccaa tgtctcgcac tgggtgcagc aagacgcgcc cgacgaagtg     840
aacgcgatcc tgcgcgagtg gctgcctaag cccgctccgg catcctga                  888

<210> SEQ ID NO 19
<211> LENGTH: 36
<212> TYPE: DNA
```

```
<213> ORGANISM: Artificial Sequence
<220> FEATURE:
<223> OTHER INFORMATION: Forward primer for Sphingopyxis alaskensis
      (SPF1)

<400> SEQUENCE: 19
cgacccggca tatgtccccc gccaaatcaa tttcgc                               36

<210> SEQ ID NO 20
<211> LENGTH: 35
<212> TYPE: DNA
<213> ORGANISM: Artificial Sequence
<220> FEATURE:
<223> OTHER INFORMATION: Reverse primer for Sphingopyxis alaskensis
      (SPRH1)

<400> SEQUENCE: 20
ctccacatgc ggccgccttc ttctcgcgca agggg                                35

<210> SEQ ID NO 21
<211> LENGTH: 36
<212> TYPE: DNA
<213> ORGANISM: Artificial Sequence
<220> FEATURE:
<223> OTHER INFORMATION: Forward primer for Novosphingobium
      aromaticivorans (NVF1)

<400> SEQUENCE: 21
cgacccggca tatgaatgtt gcgcctttcg ttgtcg                               36

<210> SEQ ID NO 22
<211> LENGTH: 36
<212> TYPE: DNA
<213> ORGANISM: Artificial Sequence
<220> FEATURE:
<223> OTHER INFORMATION: Reverse primer for Novosphingobium
      aromaticivorans (NVRH1)

<400> SEQUENCE: 22
ctccacatgc ggccgcgcac atcagggaaa acgcgg                               36

<210> SEQ ID NO 23
<211> LENGTH: 44
<212> TYPE: DNA
<213> ORGANISM: Artificial Sequence
<220> FEATURE:
<223> OTHER INFORMATION: Forward primer for Rhodobacterales bacterium
      HTCC2654 (RBF2)

<400> SEQUENCE: 23
cgacccggca tatgaacgac aagaccttta tcgagacgaa cggc                      44

<210> SEQ ID NO 24
<211> LENGTH: 44
<212> TYPE: DNA
<213> ORGANISM: Artificial Sequence
<220> FEATURE:
<223> OTHER INFORMATION: Forward primer for Rhodobacterales bacterium
      HTCC2654 (RBRH2)

<400> SEQUENCE: 24
ctccacatct cgagttacaa ggctgaaaag aacactcgca aatc                      44

<210> SEQ ID NO 25
<211> LENGTH: 37
<212> TYPE: DNA
<213> ORGANISM: Artificial Sequence
<220> FEATURE:
```

```
<223> OTHER INFORMATION: Reverse primer for sEEH without His-tag
      (SPRNH1)

<400> SEQUENCE: 25
ctccacatgc ggccgctcac ttcttctcgc gcaaggg                              37

<210> SEQ ID NO 26
<211> LENGTH: 38
<212> TYPE: DNA
<213> ORGANISM: Artificial Sequence
<220> FEATURE:
<223> OTHER INFORMATION: Reverse primer for nEEH without His-tag
      (NVRNH1)

<400> SEQUENCE: 26
ctccacatgc ggccgcctag cacatcaggg aaaacgcg                             38

<210> SEQ ID NO 27
<211> LENGTH: 40
<212> TYPE: DNA
<213> ORGANISM: Artificial Sequence
<220> FEATURE:
<223> OTHER INFORMATION: Reverse primer for rEEH without His-tag
      (RBRNH2)

<400> SEQUENCE: 27
ctccacatct cgagtcaaag cgtggcgagc cagtcgatga                           40

<210> SEQ ID NO 28
<211> LENGTH: 448
<212> TYPE: PRT
<213> ORGANISM: Erythrobacter litoralis

<400> SEQUENCE: 28
```

Met Ser Pro Ala Lys Ser Ile Ser Leu Arg Arg Leu Leu Ser Thr Ala
1               5                   10                  15

Ile Ser Val Ala Ala Leu Gly Met Thr Leu Gln Ser Pro Ser Phe
            20                  25                  30

Ala Ser Ser Ala Gly Pro Ser Thr Ala Ile Thr Val Ser Ala Ala Ala
        35                  40                  45

Ala Val Ala Ala Pro Gln Asp Glu Ser Ile Arg Pro Phe His Val Ser
    50                  55                  60

Ile Pro Glu Glu Ala Leu Thr Asp Leu Arg Arg Leu Ala Glu Thr
65                  70                  75                  80

Arg Trp Pro Asp Arg Glu Lys Val Ser Asp Ala Ser Gln Gly Val Gln
                85                  90                  95

Leu Asp Arg Leu Glu Pro Leu Val Arg Tyr Trp Gly Thr Asp Tyr Asp
            100                 105                 110

Trp Arg Lys Gly Glu Ala Arg Leu Asn Ala Val Pro Gln Phe Ile Thr
        115                 120                 125

Thr Ile Asp Gly Leu Asp Ile Gln Phe Ile His Ile Arg Ser Lys His
    130                 135                 140

Lys Gly Ala Met Pro Leu Leu Met Thr His Gly Trp Pro Gly Ser Pro
145                 150                 155                 160

Phe Glu Leu Leu Lys Thr Val Gly Pro Leu Thr Asp Pro Thr Ala His
                165                 170                 175

Gly Gly Lys Ala Glu Asp Ala Phe Asp Leu Ile Met Pro Thr Tyr Pro
            180                 185                 190

Gly Tyr Gly Phe Ser Gly Lys Pro Asn Glu Ala Trp Asp Pro Ala Arg
        195                 200                 205

```
Val Ala Arg Ala Trp Asp Val Leu Met Lys Arg Leu Gly Tyr Lys Asn
        210                 215                 220
Tyr Val Ser Gln Gly Gly Asp Trp Gly Ala Ile Ile Ser Gln Val Leu
225                 230                 235                 240
Ala Val Gln Ala Pro Glu Gly Leu Leu Gly Ile His Thr Asn Met Pro
            245                 250                 255
Gly Thr Val Pro Pro Gly Val Leu Lys Leu Val Arg Ala Lys Gln Pro
            260                 265                 270
Ala Pro Asp Ser Tyr Ser Pro Glu Glu Lys Ile Ala Tyr Ala Gly Leu
            275                 280                 285
Glu Thr Phe Tyr Gly Lys Gly Phe Gly Tyr Ala Glu Met Met Asn Thr
            290                 295                 300
Arg Pro Gln Thr Leu Gly Tyr Gly Leu Ser Asp Ser Pro Val Gly Leu
305                 310                 315                 320
Ala Ala Phe Leu Tyr Glu Lys Ile Ala Thr Trp Thr Asp Ser Gly Gly
            325                 330                 335
Asn Pro Glu Ser Val Leu Thr Arg Asp Glu Ile Leu Asp Asn Ile Thr
            340                 345                 350
Leu Tyr Trp Leu Thr Asn Thr Gly Thr Ser Ser Ser Arg Ser Tyr Trp
            355                 360                 365
Asp Ala Ala Gln Gly Pro Gly Gly Pro Phe Asn Ala Ile Glu Ile Ser
            370                 375                 380
Lys Val Pro Val Ala Val Thr Val Phe Pro Gly Glu Ile Tyr Arg Ala
385                 390                 395                 400
Pro Arg Ser Trp Gly Lys Ser Phe Lys Lys Leu Ile Tyr Trp Asn
            405                 410                 415
Glu Val Asp Lys Gly Gly His Phe Ala Ala Trp Glu Gln Pro Glu Leu
            420                 425                 430
Phe Ala Ala Glu Ile Arg Ala Ala Phe Arg Pro Leu Arg Glu Lys Lys
            435                 440                 445

<210> SEQ ID NO 29
<211> LENGTH: 1347
<212> TYPE: DNA
<213> ORGANISM: Erythrobacter litoralis

<400> SEQUENCE: 29
atgtcccccg ccaaatcaat ttcgctccgc cgcctgctgt ccaccgccat ttctgtcgcg    60
gcgctcggca tgaccctcca gtccagcccg agcttcgcca gcagcgctgg cccgtccacc   120
gctatcacgg tctcggccgc tgcggcggtc gccgcaccgc aagacgagtc catccgcccg   180
tttcatgtga gcatccccga agaggcgctc acggatcttc gccgcgtct cgccgagacg   240 cgctggcccg atcgcgaaaa ggtttcggac gcatcgcagg tgtgcaact cgaccgtctc   300 gaacccctcg tccgttattg ggcactgac tatgactggc gcaagggcga agccgcctc    360 aacgccgtgc gcagttcat caccaccatc gacggtctcg catccagtt catccacatc   420 cgctcgaagc ataagggtgc gatgccgctg ctcatgacgc acggctggcc cggctcaccg   480
ttcgagctgc tgaaaaccgt cggaccgctt accgatccga ccgcgcacgg cgggaaggcc   540
gaagacgcct cgacctgat catgccgacc tatccgggtt atgggttttc ggcaagccg    600 aacgaggcat gggatccggc cgggtggcg cgcgcctggg atgtgctgat gaagcgtctc   660
ggctacaaga attatgtgtc gcaggcggc gattggggcg cgatcatttc gcaggtgctg   720
gccgtgcagg cacccgaagg attgcttggc atccatacca atatgccggg caccgttccg   780
ccgggcgttc tcaagctcgt ccgcgccaag caaccggctc cggacagcta ttctcccgaa   840
```

```
gagaagatcg cctacgccgg tctcgagacc ttctacggca agggcttcgg ctatgccgaa      900
atgatgaaca cgcgcccgca gacgctcggc tacggcctgt cggactctcc ggtcgggctt      960
gcagctttcc tctacgagaa gatcgcgacc tggacggata cggtggcaa tcccgaaagc      1020 gtgctgacgc gcgacgagat actcgacaac atcacccttt actggctgac caacaccgga      1080
acctcgtcat cgcgcagcta ttgggatgcc gcgcagggcc cgggcggtcc gttcaacgcg      1140
atcgagatca gcaaggtgcc ggtcgcggtg accgtcttcc ccggcgagat ctatcgcgcg      1200
ccgcgcagct ggggcgaaaa gagcttcaag aagctcatct actggaacga ggtcgacaag      1260
ggcggtcatt tcgccgcctg ggaacagccc gagctgttcg ctgccgagat ccgcgccgcc      1320
ttccgcccct tgcgcgagaa gaagtga                                          1347
```

<210> SEQ ID NO 30
<211> LENGTH: 377
<212> TYPE: PRT
<213> ORGANISM: Erythrobacter litoralis

<400> SEQUENCE: 30

```
Met Asn Val Ala Pro Phe Val Val Asp Ile Pro Arg Gly Glu Ile Glu
1               5                   10                  15

Asp Leu His Arg Arg Ile Asp Met Thr Arg Trp Pro Glu Lys Glu Thr
            20                  25                  30

Val Asp Trp Ser Gln Gly Thr Pro Leu Gly Ala Leu Gln Asp Phe
        35                  40                  45

Val Ser Tyr Trp Arg Gly Gly Tyr Asp Trp Tyr Ala Cys Gln Arg Met
    50                  55                  60

Leu Asn Asp Trp Gly Met Phe Glu Thr Glu Ile Asp Gly Val Ala Ile
65                  70                  75                  80

Arg Phe Leu His Val Arg Ser Ala Gln Ala Asp Ala Arg Pro Leu Leu
                85                  90                  95

Leu Thr His Gly Trp Pro Gly Ser Ile Leu Glu Phe Arg Arg Cys Ile
            100                 105                 110

Ala Pro Leu Thr Arg Pro Glu Glu His Gly Gly Thr Ala Ala Asp Ala
        115                 120                 125

Phe His Leu Val Ile Pro Cys Leu Pro Gly Tyr Gly Phe Ser Gly Lys
    130                 135                 140

Pro Thr Arg Lys Gly Trp Ser Val Gln Lys Ile Ala Gln Ala Trp Gly
145                 150                 155                 160

Glu Leu Met Lys Arg Leu Gly Tyr Glu Ser Trp Leu Ala Gln Gly Gly
                165                 170                 175

Asp Trp Gly Ser Ala Val Thr Thr Ala Ile Gly Ala Leu Lys Val Glu
            180                 185                 190

Gly Cys Ala Gly Ile His Leu Asn Met Pro Ile Ala Arg Pro Leu Pro
        195                 200                 205

Glu Asp Leu Ala Ala Pro Thr Pro Glu Glu Leu Arg Ala Leu Thr Ala
    210                 215                 220

Leu Gln His Tyr Gln Asp Trp Asp Ser Gly Tyr Ser Lys Glu Gln Ala
225                 230                 235                 240

Thr Arg Pro Gln Thr Val Gly Tyr Gly Leu Val Asp Ser Pro Val Gly
                245                 250                 255

Leu Ala Gly Trp Ile Tyr Glu Lys Met Trp Ala Trp Thr Asp Asn Glu
            260                 265                 270

Gly Ala Pro Glu Asp Ala Leu Ser Arg Asp Asp Met Leu Asp Asn Ile
        275                 280                 285
```

```
Met Leu Tyr Trp Leu Thr Ala Ala Gly Ala Ser Ser Ala Arg Leu Tyr
    290                 295                 300

Trp Glu Ser Phe Ala Ser Phe Gly Pro Ser Gln Ile Asp Ile Pro Ala
305                 310                 315                 320

Ala Ala Ser Ala Phe Pro Lys Glu Ile Ile Pro Ala Pro Arg Lys Trp
                325                 330                 335

Phe Glu Arg Asn Cys Ser Lys Leu Val Tyr Trp Gly Glu Leu Glu Lys
            340                 345                 350

Gly Gly His Phe Ala Ala Trp Glu Gln Pro Glu Ala Phe Val Lys Glu
        355                 360                 365

Leu Arg Ala Ala Phe Ser Leu Met Cys
    370                 375

<210> SEQ ID NO 31
<211> LENGTH: 1134
<212> TYPE: DNA
<213> ORGANISM: Erythrobacter litoralis

<400> SEQUENCE: 31
atgaatgttg cgccttctcgt tgtcgacata cctcgcggcg agatcgagga cctgcatcgt      60
cgcatcgaca tgacacgctg gcccgagaaa gagacggtcg acgactggtc gcagggcacg     120
ccgcttggcg cgttgcagga tttcgtgagc tactggcgcg cggctatga ctggtacgcg      180 tgccagagga tgctgaacga ctgggcatg ttcgagaccg agatcgacgg agtggcgatc      240
cgcttcctcc acgtgcgctc tgcgcaagca gatgcgcggc cctgctgct gacccacggc      300 tggccgggat cgattctcga gttccgccgc tgcatcgcgc cgctgacccg cccagaggag     360
catggtggta ctgccgccga cgcgttccat ctcgtgatcc cttgcctgcc gggatacggc     420
ttttccggaa agcccacgcg caagggctgg agcgtgcaga gatcgcgca ggcctgggc      480 gaactgatga gcggctggg ctacgaaagc tggcttgcac agggcgggga ctggggttcc     540
gccgttacca ctgccatcgg ggcgctgaag gtggaggct gcgcgggcat ccatctcaac     600
atgccgatcg cccggcccct gccggaggac ctggccgctc cgacgccgga ggagctaagg    660
gcgctgaccg cgctacagca ctatcaggat tgggattcgg ggtattccaa ggagcaggcg     720
acccggcccc agacggtagg ttacgggctg gtcgattcgc cggtcgggct ggctggctgg    780
atctacgaga agatgtgggc ctggaccgac aacgaggcg cgcccgagga cgcgctgagc      840
cgcgacgaca tgctcgacaa catcatgctg tactggctga cggcggcagg gcatcgtcg     900 gcccggcttt attgggagag ttttgcgagc ttcgggccat cgcagatcga cattccggcc    960
gcggccagcg cctttccgaa ggagataatt cccgcgccgc gcaagtggtt cgagcgcaac   1020
tgttcgaagc tggtctactg gggcgagctg gaaaagggcg gccactttgc cgcgtgggag   1080
cagcccgaag ccttcgtgaa ggaacttcgg gccgcgtttt ccctgatgtg ctag          1134

<210> SEQ ID NO 32
<211> LENGTH: 320
<212> TYPE: PRT
<213> ORGANISM: Erythrobacter litoralis

<400> SEQUENCE: 32

Met Asn Asp Lys Thr Phe Ile Glu Thr Asn Gly Ile Arg Leu Ala Thr
1               5                  10                  15

Arg Ile Glu Gly Asp Gly Pro Leu Val Ile Leu Val His Gly Phe Pro
            20                  25                  30

Glu Thr Ala Tyr Ser Trp Arg Lys Gln Ala Ser Pro Leu Val Glu Ala
```

|   |   |   | 35 |   |   |   | 40 |   |   |   | 45 |   |   |
|---|---|---|---|---|---|---|---|---|---|---|---|---|---|

Gly Tyr Arg Val Cys Ile Pro Asp Val Arg Gly Tyr Gly Asn Ser Asp
 50                  55                  60

Ala Pro Glu Ala Val Ser Ala Tyr Ala Met Glu Val Met Thr Arg Asp
 65                  70                  75                  80

Phe Leu Gly Leu Ala Gln Ala Leu Ser Glu Val Pro Ala Val Ile Val
                 85                  90                  95

Gly His Asp Trp Gly Ala Pro Leu Ala Trp Asn Thr Ala Arg Leu Phe
                100                 105                 110

Pro Glu Gln Phe Arg Ala Val Ala Gly Leu Ser Val Pro Tyr Ala Pro
            115                 120                 125

Pro Gly Asp Val Ala Pro Ile Asp Leu Tyr His Lys Leu Phe Thr Asp
    130                 135                 140

Lys Gly Arg Phe Phe Tyr Gln Val Tyr Phe Gln Asp Glu Gly Val Ala
145                 150                 155                 160

Glu Ala Glu Leu Glu Ala Asp Val Glu Asp Ser Leu Ala Lys Phe Tyr
                165                 170                 175

Tyr Ala Trp Ser Gly Asp Cys Pro Pro Asn Gly Trp Pro Asn Asp Lys
            180                 185                 190

Ala His Gly Asp Pro Val Leu Lys Gly Leu Pro Arg Pro Asp Leu Pro
    195                 200                 205

Leu Pro Trp Leu Thr Gln Asp Asp Leu Asp Arg Tyr Ala Ala Asp Phe
210                 215                 220

Arg Thr Ser Gly Phe Arg Gly Pro Leu Asn Arg Tyr Arg Asn Gln Arg
225                 230                 235                 240

Glu Asp His Ala Phe Leu Lys Ala His Pro Ser Asn Pro Ile Ile Gln
                245                 250                 255

Gln Pro Ser Leu Phe Leu Tyr Gly Asp Arg Asp Pro Val Leu Thr Met
            260                 265                 270

Phe Arg Thr Pro Pro Glu Asp Leu Leu Pro Lys Thr Leu Ala Asp Leu
    275                 280                 285

Arg Gly Val His Arg Leu Pro Gly Val Gly His Trp Thr Gln Gln Glu
290                 295                 300

Ala Pro Glu Ala Val Asn Lys Ala Leu Ile Asp Trp Leu Ala Thr Leu
305                 310                 315                 320

<210> SEQ ID NO 33
<211> LENGTH: 963
<212> TYPE: DNA
<213> ORGANISM: Erythrobacter litoralis

<400> SEQUENCE: 33
atgaacgaca agacctttat cgagacgaac ggcattcggc tggccacgcg catcgagggc          60
gacgggccgc tcgtcatcct cgtccacggc tttcccgaga ccgcgtatag ctggcgcaag         120
caggcgtcgc cgctggtgga agcgggctac cgcgtgtgta ttcccgatgt acgcggctac         180
ggcaattcgg acgcgccgga ggccgttttcg gcctatgcga tggaggtcat gacgcgcgac        240
tttctgggtc tcgcgcaggc gttgtcggaa gtacccgccg tcattgtcgg catgactgg          300 ggcgcgccct ggcatggaa caccgcgcgg ctcttccctg agcagtttcg cgccgtcgct          360
gggctttccg tgccctacgc accacctggc gacgtcgcgc cgatcgacct ttaccacaag         420
cttttcaccg acaagggccg cttcttctat caggtctatt ttcaggacga gggcgtggcc         480
gaagccgagt tggaggcgga tgtcgaagac agcctcgcca gttttactac gcgcggtcc          540 ggcgactgcc cgccgaacgg atggcccaac gacaaggcgc acggcgaccc ggtgctcaag         600

```
ggcctgcccc ggcccgatct gccgctgccg tggctgacgc aagatgacct cgaccgctac    660
gccgcagatt tccgcacctc cgggtttcgt ggcccgctca accgataccg aaatcagcgg    720
gaggatcacg cgtttctcaa agcgcatccg tcgaacccga tcatccagca gccgagcctg    780
ttcctttatg gcgaccgtga cccggtgctg accatgttcc gcaccccgcc cgaggatctt    840
ctgcccaaga cgctggccga cctgcgcggc gtgcaccgcc tgcccggtgt cggccactgg    900
acccagcagg aagcgcccga agcggtcaac aaggcgctca tcgactggct cgccacgctt    960
tga                                                                  963
```

<210> SEQ ID NO 34
<211> LENGTH: 409
<212> TYPE: PRT
<213> ORGANISM: Rhodotorula glutinis

<400> SEQUENCE: 34

```
Met Ala Thr His Thr Phe Ala Ser Pro Pro Thr Arg Phe Thr Val Asp
 1               5                  10                  15

Ile Pro Gln Ser Glu Leu Asp Glu Leu His Ser Arg Leu Asp Lys Thr
                20                  25                  30

Arg Trp Pro Ala Thr Glu Ile Val Pro Glu Asp Gly Thr Asp Asp Pro
            35                  40                  45

Thr Ala Phe Gly Leu Gly Ala Gly Pro Thr Leu Pro Leu Met Lys Glu
        50                  55                  60

Leu Ala Lys Gly Trp Arg Glu Phe Asp Trp Lys Lys Ala Gln Asp His
    65                  70                  75                  80

Leu Asn Thr Phe Glu His Tyr Met Val Glu Ile Glu Asp Leu Ser Ile
                85                  90                  95

His Phe Leu His His Arg Ser Thr Arg Pro Asn Ala Val Pro Leu Ile
                100                 105                 110

Leu Cys His Gly Trp Pro Gly His Phe Gly Glu Phe Leu Asn Val Ile
            115                 120                 125

Pro Leu Leu Thr Glu Pro Ser Asp Pro Ser Ala Gln Ala Phe His Val
        130                 135                 140

Val Ala Pro Ser Met Pro Gly Tyr Ala Trp Ser Leu Pro Pro Pro Ser
145                 150                 155                 160

Ser Lys Trp Asn Met Pro Asp Thr Ala Arg Val Phe Asp Lys Leu Met
                165                 170                 175

Thr Gly Leu Gly Tyr Glu Lys Tyr Met Ala Gln Gly Gly Asp Trp Gly
            180                 185                 190

Ser Ile Ala Ala Arg Cys Leu Gly Ser Leu His Lys Asp His Cys Lys
        195                 200                 205

Ala Val His Leu Asn Phe Leu Pro Val Phe Pro Val Pro Met Trp
    210                 215                 220

Leu Ile Asn Pro His Thr Leu Leu Ala Trp Ala Pro Arg Phe Leu Val
225                 230                 235                 240

Pro Glu Lys Gln Ala Ala Arg Met Lys Arg Gly Leu Ala Tyr Leu Glu
                245                 250                 255

Lys Gly Ser Ala Tyr Tyr Val Met Gln Gln Leu Thr Pro Arg Thr Pro
            260                 265                 270

Ala Tyr Gly Leu Thr Asp Ser Pro Val Gly Leu Leu Ala Trp Ile Gly
        275                 280                 285

Glu Lys Phe Glu Pro Thr Ile Gln Glu Ala Ser Lys Gln Ala Gln Pro
    290                 295                 300
```

```
Thr Leu Thr Arg Asp Glu Leu Tyr Phe Thr Cys Ser Leu Tyr Trp Phe
305                 310                 315                 320

Thr Arg Ser Ile Gly Thr Ser Phe Leu Pro Tyr Ser Leu Asn Pro His
            325                 330                 335

Phe Thr Thr Phe Leu Thr Asp Ser Lys Tyr His Leu Pro Asn Phe Ala
        340                 345                 350

Leu Ser Leu Tyr Pro Gly Glu Ile Tyr Cys Pro Ala Glu Arg Asp Ala
    355                 360                 365

Lys Arg Thr Gly Asn Leu Lys Trp Ile Lys Asp Ala Pro Glu Gly Gly
370                 375                 380

His Phe Ala Ala Leu Glu Lys Pro Asp Val Phe Val Glu His Leu Arg
385                 390                 395                 400

Glu Ala Phe Gly Val Met Trp Glu Lys
                405
```

<210> SEQ ID NO 35
<211> LENGTH: 398
<212> TYPE: PRT
<213> ORGANISM: Aspergillus niger

<400> SEQUENCE: 35

```
Met Ser Ala Pro Phe Ala Lys Phe Pro Ser Ser Ala Ser Ile Ser Pro
1               5                   10                  15

Asn Pro Phe Thr Val Ser Ile Pro Asp Glu Gln Leu Asp Asp Leu Lys
            20                  25                  30

Thr Leu Val Arg Leu Ser Lys Ile Ala Pro Pro Thr Tyr Glu Ser Leu
        35                  40                  45

Gln Ala Asp Gly Arg Phe Gly Ile Thr Ser Glu Trp Leu Thr Thr Met
    50                  55                  60

Arg Glu Lys Trp Leu Ser Glu Phe Asp Trp Arg Pro Phe Glu Ala Arg
65                  70                  75                  80

Leu Asn Ser Phe Pro Gln Phe Thr Thr Glu Ile Glu Gly Leu Thr Ile
                85                  90                  95

His Phe Ala Ala Leu Phe Ser Glu Arg Glu Asp Ala Val Pro Ile Ala
            100                 105                 110

Leu Leu His Gly Trp Pro Gly Ser Phe Val Glu Phe Tyr Pro Ile Leu
        115                 120                 125

Gln Leu Phe Arg Glu Glu Tyr Thr Pro Glu Thr Leu Pro Phe His Leu
    130                 135                 140

Val Val Pro Ser Leu Pro Gly Tyr Thr Phe Ser Ser Gly Pro Pro Leu
145                 150                 155                 160

Asp Lys Asp Phe Gly Leu Met Asp Asn Ala Arg Val Val Asp Gln Leu
                165                 170                 175

Met Lys Asp Leu Gly Phe Gly Ser Gly Tyr Ile Ile Gln Gly Gly Asp
            180                 185                 190

Ile Gly Ser Phe Val Gly Arg Leu Leu Gly Val Gly Phe Asp Ala Cys
        195                 200                 205

Lys Ala Val His Leu Asn Leu Cys Ala Met Arg Ala Pro Pro Glu Gly
    210                 215                 220

Pro Ser Ile Glu Ser Leu Ser Ala Ala Glu Lys Glu Gly Ile Ala Arg
225                 230                 235                 240

Met Glu Lys Phe Met Thr Asp Gly Leu Ala Tyr Ala Met Glu His Ser
                245                 250                 255

Thr Arg Pro Ser Thr Ile Gly His Val Leu Ser Ser Pro Ile Ala
            260                 265                 270
```

```
Leu Leu Ala Trp Ile Gly Glu Lys Tyr Leu Gln Trp Val Asp Lys Pro
            275                 280                 285

Leu Pro Ser Glu Thr Ile Leu Glu Met Val Ser Leu Tyr Trp Leu Thr
290                 295                 300

Glu Ser Phe Pro Arg Ala Ile His Thr Tyr Arg Glu Thr Thr Pro Thr
305                 310                 315                 320

Ala Ser Ala Pro Asn Gly Ala Thr Met Leu Gln Lys Glu Leu Tyr Ile
            325                 330                 335

His Lys Pro Phe Gly Phe Ser Phe Phe Pro Lys Asp Leu Cys Pro Val
            340                 345                 350

Pro Arg Ser Trp Ile Ala Thr Thr Gly Asn Leu Val Phe Phe Arg Asp
            355                 360                 365

His Ala Glu Gly Gly His Phe Ala Ala Leu Glu Arg Pro Arg Glu Leu
370                 375                 380

Lys Thr Asp Leu Thr Ala Phe Val Glu Gln Val Trp Gln Lys
385                 390                 395

<210> SEQ ID NO 36
<211> LENGTH: 411
<212> TYPE: PRT
<213> ORGANISM: Xanthophyllomyces dendrorhous

<400> SEQUENCE: 36

Met Thr Ser Ala Asn Ile Pro Thr Pro Phe Gln Val Ser Phe Ala Gln
1               5                   10                  15

Gln Asp Val Asp Arg Met Met Ala Lys Ile Arg Asp Thr Arg Leu Pro
            20                  25                  30

Thr Ala Pro Ile Val Pro Gly Ala Ser Trp Asp Tyr Gly Ile Asp Leu
        35                  40                  45

Asp Trp Leu Thr Glu Leu His Lys Tyr Trp Ala Asn Glu Trp Ser Trp
50                  55                  60

Glu Glu Thr Glu Lys Arg Ile Asn Lys Tyr Pro His Phe Arg Val Asp
65                  70                  75                  80

Ile Glu Glu Ile Ser Leu His Phe Val His Ile Lys Ser Lys Gln Pro
                85                  90                  95

Asp Ala Ile Pro Leu Ile Leu Ser His Gly Trp Pro Ser Ser Phe Leu
            100                 105                 110

Glu Phe Trp Glu Val Ile Asp Glu Leu Val Asp Pro Thr Lys Ala Gly
            115                 120                 125

Gln Pro Ala Phe His Val Val Ile Pro Ser Met Pro Gly Tyr Thr Phe
130                 135                 140

Ser Ser Gly Pro Gln Arg Lys Gly Trp Thr Val Val Asp Thr Ala Arg
145                 150                 155                 160

Val Tyr Asn Ser Leu Met Val Asn Val Leu Gly Tyr Lys Thr Tyr Thr
                165                 170                 175

Cys Gly Ala Gly Asp Trp Gly Ser Trp Ile Thr Ala Gln Ile Leu His
            180                 185                 190

Asp Tyr Ser Glu Phe Ala Val Val Ala His Phe Thr Met Ile Lys Ala
        195                 200                 205

Ser Val Pro Ile Leu Asn Pro Ile Tyr Ser Leu Pro Ile Leu Leu Gly
210                 215                 220

Lys Ile Pro Phe Val Pro Lys Gly Val Ala Arg Trp Leu Gln Ser Leu
225                 230                 235                 240

Val Tyr Thr Glu Ala Glu Ile Asn Gly Leu Glu Arg Thr Asp Lys Phe
                245                 250                 255
```

```
Trp Lys Glu Gly Leu Gly Tyr Gln Lys Ile Gln Gly Ser Lys Pro Met
            260                 265                 270

Thr Leu Gly Ala Ala Leu Phe Asp Ser Pro Val Gly Ile Leu Ser Trp
        275                 280                 285

Ile Gly Glu Lys Tyr His Gly Trp Ser Asp Pro Arg Ala Pro Ser Ala
    290                 295                 300

Pro Ser Gln Val Thr Pro Asn His Ile Val Thr Val Thr Ala Leu Tyr
305                 310                 315                 320

Phe Leu Thr Gly Ser Ile His Thr Ser Phe Leu Pro Tyr Lys Glu Tyr
                325                 330                 335

Thr Leu Ser Pro Met Ala Val Ala Val Gly Lys Lys Arg Pro Ile Gly
            340                 345                 350

Leu Ser Ile Phe Pro Ala Glu Ile Thr Gln Tyr Pro Arg Ser Trp Val
        355                 360                 365

Ala Ser Ser Cys Lys Leu Val Asn Tyr Lys Val His Ala Arg Gly Gly
    370                 375                 380

His Phe Ala Ala Val Asp Asn Pro Gly Ala Tyr Val Glu Asp Ile Arg
385                 390                 395                 400

Glu Thr Ile Gly Lys Asn Tyr His Ser Glu Leu
                405                 410

<210> SEQ ID NO 37
<211> LENGTH: 455
<212> TYPE: PRT
<213> ORGANISM: Homo sapiens

<400> SEQUENCE: 37

Met Trp Leu Glu Ile Leu Leu Thr Ser Val Leu Gly Phe Ala Ile Tyr
1               5                   10                  15

Trp Phe Ile Ser Arg Asp Lys Glu Glu Thr Leu Pro Leu Glu Asp Gly
            20                  25                  30

Trp Trp Gly Pro Gly Thr Arg Ser Ala Ala Arg Glu Asp Asp Ser Ile
        35                  40                  45

Arg Pro Phe Lys Val Glu Thr Ser Asp Glu Glu Ile His Asp Leu His
50                  55                  60

Gln Arg Ile Asp Lys Phe Arg Phe Thr Pro Pro Leu Glu Asp Ser Cys
65                  70                  75                  80

Phe His Tyr Gly Phe Asn Ser Asn Tyr Leu Lys Lys Val Ile Ser Tyr
                85                  90                  95

Trp Arg Asn Glu Phe Asp Trp Lys Lys Gln Val Glu Ile Leu Asn Arg
            100                 105                 110

Tyr Pro His Phe Lys Thr Lys Ile Glu Gly Leu Asp Ile His Phe Ile
        115                 120                 125

His Val Lys Pro Pro Gln Leu Pro Ala Gly His Thr Pro Lys Pro Leu
130                 135                 140

Leu Met Val His Gly Trp Pro Gly Ser Phe Tyr Glu Phe Tyr Lys Ile
145                 150                 155                 160

Ile Pro Leu Leu Thr Asp Pro Lys Asn His Gly Leu Ser Asp Glu His
                165                 170                 175

Val Phe Glu Val Ile Cys Pro Ser Ile Pro Gly Tyr Gly Phe Ser Glu
            180                 185                 190

Ala Ser Ser Lys Lys Gly Phe Asn Ser Val Ala Thr Ala Arg Ile Phe
        195                 200                 205

Tyr Lys Leu Met Leu Arg Leu Gly Phe Gln Glu Phe Tyr Ile Gln Gly
    210                 215                 220
```

```
Gly Asp Trp Gly Ser Leu Ile Cys Thr Asn Met Ala Gln Leu Val Pro
225                 230                 235                 240

Ser His Val Lys Gly Leu His Leu Asn Met Ala Leu Val Leu Ser Asn
            245                 250                 255

Phe Ser Thr Leu Thr Leu Leu Leu Gly Gln Arg Phe Gly Arg Phe Leu
        260                 265                 270

Gly Leu Thr Glu Arg Asp Val Glu Leu Leu Tyr Pro Val Lys Glu Lys
    275                 280                 285

Val Phe Tyr Ser Leu Met Arg Glu Ser Gly Tyr Met His Ile Gln Cys
290                 295                 300

Thr Lys Pro Asp Thr Val Gly Ser Ala Leu Asn Asp Ser Pro Val Gly
305                 310                 315                 320

Leu Ala Ala Tyr Ile Leu Glu Lys Phe Ser Thr Trp Thr Asn Thr Glu
            325                 330                 335

Phe Arg Tyr Leu Glu Asp Gly Gly Leu Glu Arg Lys Phe Ser Leu Asp
        340                 345                 350

Asp Leu Leu Thr Asn Val Met Leu Tyr Trp Thr Thr Gly Thr Ile Ile
    355                 360                 365

Ser Ser Gln Arg Phe Tyr Lys Glu Asn Leu Gly Gln Gly Trp Met Thr
370                 375                 380

Gln Lys His Glu Arg Met Lys Val Tyr Val Pro Thr Gly Phe Ser Ala
385                 390                 395                 400

Phe Pro Phe Glu Leu Leu His Thr Pro Glu Lys Trp Val Arg Phe Lys
            405                 410                 415

Tyr Pro Lys Leu Ile Ser Tyr Ser Tyr Met Val Arg Gly His Phe
        420                 425                 430

Ala Ala Phe Glu Glu Pro Glu Leu Leu Ala Gln Asp Ile Arg Lys Phe
    435                 440                 445

Leu Ser Val Leu Glu Arg Gln
    450                 455

<210> SEQ ID NO 38
<211> LENGTH: 455
<212> TYPE: PRT
<213> ORGANISM: Rattus norvegicus

<400> SEQUENCE: 38

Met Trp Leu Glu Leu Val Leu Ala Ser Leu Leu Gly Phe Val Ile Tyr
1               5                   10                  15

Trp Phe Val Ser Arg Asp Lys Glu Glu Thr Leu Pro Leu Gly Asp Gly
            20                  25                  30

Trp Trp Gly Pro Gly Ser Lys Pro Ser Ala Lys Glu Asp Glu Ser Ile
        35                  40                  45

Arg Pro Phe Lys Val Glu Thr Ser Asp Glu Glu Ile Lys Asp Leu His
    50                  55                  60

Gln Arg Ile Asp Arg Phe Arg Ala Ser Pro Pro Leu Glu Gly Ser Arg
65                  70                  75                  80

Phe His Tyr Gly Phe Asn Ser Asn Tyr Met Lys Lys Val Val Ser Tyr
            85                  90                  95

Trp Arg Asn Glu Phe Asp Trp Arg Lys Gln Val Glu Ile Leu Asn Gln
        100                 105                 110

Tyr Pro His Phe Lys Thr Lys Ile Glu Gly Leu Asp Ile His Phe Ile
    115                 120                 125

His Val Lys Pro Pro Gln Leu Pro Ser Gly Arg Thr Pro Lys Pro Leu
130                 135                 140
```

```
Leu Met Val His Gly Trp Pro Gly Ser Phe Tyr Glu Phe Tyr Lys Ile
145                 150                 155                 160

Ile Pro Leu Leu Thr Asp Pro Lys Ser His Gly Leu Ser Asp Glu His
            165                 170                 175

Val Phe Glu Val Ile Cys Pro Ser Ile Pro Gly Tyr Gly Tyr Ser Glu
        180                 185                 190

Ala Ser Ser Lys Lys Gly Leu Asn Ser Val Ala Thr Ala Arg Ile Phe
    195                 200                 205

Tyr Lys Leu Met Thr Arg Leu Gly Phe Gln Lys Phe Tyr Ile Gln Gly
210                 215                 220

Gly Asp Trp Gly Ser Leu Ile Cys Thr Asn Met Ala Gln Met Val Pro
225                 230                 235                 240

Asn His Val Lys Gly Leu His Leu Asn Met Ala Phe Ile Ser Arg Ser
                245                 250                 255

Phe Tyr Thr Met Thr Pro Leu Leu Gly Gln Arg Phe Gly Arg Phe Leu
            260                 265                 270

Gly Tyr Thr Glu Lys Asp Ile Glu Leu Leu Tyr Pro Tyr Lys Glu Lys
        275                 280                 285

Val Phe Tyr Ser Ile Met Arg Glu Ser Gly Tyr Leu His Ile Gln Ala
    290                 295                 300

Thr Lys Pro Asp Thr Val Gly Cys Ala Leu Asn Asp Ser Pro Val Gly
305                 310                 315                 320

Leu Ala Ala Tyr Ile Leu Glu Lys Phe Ser Thr Trp Thr Lys Ser Glu
                325                 330                 335

Tyr Arg Glu Leu Glu Asp Gly Gly Leu Glu Arg Lys Phe Ser Leu Asp
            340                 345                 350

Asp Leu Leu Val Asn Ile Met Ile Tyr Trp Thr Thr Gly Thr Ile Val
        355                 360                 365

Ser Ser Gln Arg Tyr Tyr Lys Glu Asn Leu Gly Gln Gly Ile Met Val
    370                 375                 380

His Lys His Glu Gly Met Lys Val Phe Val Pro Thr Gly Phe Ser Ala
385                 390                 395                 400

Phe Pro Ser Glu Leu Leu His Ala Pro Glu Lys Trp Val Lys Val Lys
                405                 410                 415

Tyr Pro Lys Leu Ile Ser Tyr Ser Tyr Met Glu Arg Gly Gly His Phe
            420                 425                 430

Ala Ala Phe Glu Glu Pro Lys Leu Leu Ala Gln Asp Ile Arg Lys Phe
        435                 440                 445

Val Ser Leu Ala Glu Leu Gln
    450                 455

<210> SEQ ID NO 39
<211> LENGTH: 555
<212> TYPE: PRT
<213> ORGANISM: Homo sapiens

<400> SEQUENCE: 39

Met Thr Leu Arg Ala Ala Val Phe Asp Leu Asp Gly Val Leu Ala Leu
1               5                   10                  15

Pro Ala Val Phe Gly Val Leu Gly Arg Thr Glu Glu Ala Leu Ala Leu
            20                  25                  30

Pro Arg Gly Leu Leu Asn Asp Ala Phe Gln Lys Gly Pro Glu Gly
        35                  40                  45

Ala Thr Thr Arg Leu Met Lys Gly Glu Ile Thr Leu Ser Gln Trp Ile
    50                  55                  60
```

```
Pro Leu Met Glu Glu Asn Cys Arg Lys Cys Ser Glu Thr Ala Lys Val
 65                  70                  75                  80

Cys Leu Pro Lys Asn Phe Ser Ile Lys Glu Ile Phe Asp Lys Ala Ile
                 85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
        115                 120                 125

Asp Arg Ala Glu Arg Asp Gly Leu Ala Gln Leu Met Cys Glu Leu Lys
130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
        195                 200                 205

Ala Leu Lys Glu Leu Glu Lys Val Thr Gly Ile Gln Leu Leu Asn Thr
210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Ser Gly Pro Ala Val Cys Leu Cys His Gly Phe Pro Glu Ser Trp Tyr
            260                 265                 270

Ser Trp Arg Tyr Gln Ile Pro Ala Leu Ala Gln Ala Gly Tyr Arg Val
        275                 280                 285

Leu Ala Met Asp Met Lys Gly Tyr Gly Glu Ser Ser Ala Pro Pro Glu
290                 295                 300

Ile Glu Glu Tyr Cys Met Glu Val Leu Cys Lys Glu Met Val Thr Phe
305                 310                 315                 320

Leu Asp Lys Leu Gly Leu Ser Gln Ala Val Phe Ile Gly His Asp Trp
                325                 330                 335

Gly Gly Met Leu Val Trp Tyr Met Ala Leu Phe Tyr Pro Glu Arg Val
            340                 345                 350

Arg Ala Val Ala Ser Leu Asn Thr Pro Phe Ile Pro Ala Asn Pro Asn
        355                 360                 365

Met Ser Pro Leu Glu Ser Ile Lys Ala Asn Pro Val Phe Asp Tyr Gln
370                 375                 380

Leu Tyr Phe Gln Glu Pro Gly Val Ala Glu Ala Glu Leu Glu Gln Asn
385                 390                 395                 400

Leu Ser Arg Thr Phe Lys Ser Leu Phe Arg Ala Ser Asp Glu Ser Val
                405                 410                 415

Leu Ser Met His Lys Val Cys Glu Ala Gly Gly Leu Phe Val Asn Ser
            420                 425                 430

Pro Glu Glu Pro Ser Leu Ser Arg Met Val Thr Glu Glu Glu Ile Gln
        435                 440                 445

Phe Tyr Val Gln Gln Phe Lys Lys Ser Gly Phe Arg Gly Pro Leu Asn
450                 455                 460

Trp Tyr Arg Asn Met Glu Arg Asn Trp Lys Trp Ala Cys Lys Ser Leu
465                 470                 475                 480

Gly Arg Lys Ile Leu Ile Pro Ala Leu Met Val Thr Ala Glu Lys Asp
                485                 490                 495
```

```
Phe Val Leu Val Pro Gln Met Ser Gln His Met Glu Asp Trp Ile Pro
                500                 505                 510

His Leu Lys Arg Gly His Ile Glu Asp Cys Gly His Trp Thr Gln Met
            515                 520                 525

Asp Lys Pro Thr Glu Val Asn Gln Ile Leu Ile Lys Trp Leu Asp Ser
    530                 535                 540

Asp Ala Arg Asn Pro Pro Val Val Ser Lys Met
545                 550                 555

<210> SEQ ID NO 40
<211> LENGTH: 554
<212> TYPE: PRT
<213> ORGANISM: Rattus norvegicus

<400> SEQUENCE: 40

Met Ala Leu Arg Val Ala Ala Phe Asp Leu Asp Gly Val Leu Ala Leu
1               5                   10                  15

Pro Ser Ile Ala Gly Val Leu Arg His Thr Glu Ala Leu Ala Leu
            20                  25                  30

Pro Arg Asp Phe Leu Leu Gly Ala Phe Gln Met Lys Phe Pro Glu Gly
        35                  40                  45

Pro Thr Glu Gln Leu Met Lys Gly Lys Ile Thr Phe Ser Gln Trp Val
    50                  55                  60

Pro Leu Met Asp Glu Ser Cys Arg Lys Ser Ser Lys Ala Cys Gly Ala
65                  70                  75                  80

Ser Leu Pro Glu Asn Phe Ser Ile Ser Glu Ile Phe Ser Gln Ala Met
                85                  90                  95

Ala Ala Arg Ser Ile Asn Arg Pro Met Leu Gln Ala Ala Ala Leu
            100                 105                 110

Lys Lys Lys Gly Phe Thr Thr Cys Ile Val Thr Asn Asn Trp Leu Asp
        115                 120                 125

Asp Ser Asp Lys Arg Asp Ile Leu Ala Gln Met Met Cys Glu Leu Ser
    130                 135                 140

Gln His Phe Asp Phe Leu Ile Glu Ser Cys Gln Val Gly Met Ile Lys
145                 150                 155                 160

Pro Glu Pro Gln Ile Tyr Lys Phe Val Leu Asp Thr Leu Lys Ala Lys
                165                 170                 175

Pro Asn Glu Val Val Phe Leu Asp Asp Phe Gly Ser Asn Leu Lys Pro
            180                 185                 190

Ala Arg Asp Met Gly Met Val Thr Ile Leu Val Arg Asp Thr Ala Ser
        195                 200                 205

Ala Leu Arg Glu Leu Glu Lys Val Thr Gly Thr Gln Phe Pro Glu Ala
    210                 215                 220

Pro Leu Pro Val Pro Cys Ser Pro Asn Asp Val Ser His Gly Tyr Val
225                 230                 235                 240

Thr Val Lys Pro Gly Ile Arg Leu His Phe Val Glu Met Gly Ser Gly
                245                 250                 255

Pro Ala Ile Cys Leu Cys His Gly Phe Pro Glu Ser Trp Phe Ser Trp
            260                 265                 270

Arg Tyr Gln Ile Pro Ala Leu Ala Gln Ala Gly Phe Arg Val Leu Ala
        275                 280                 285

Ile Asp Met Lys Gly Tyr Gly Asp Ser Ser Pro Pro Glu Ile Glu
    290                 295                 300

Glu Tyr Ala Met Glu Leu Leu Cys Glu Glu Met Val Thr Phe Leu Asn
305                 310                 315                 320
```

```
Lys Leu Gly Ile Pro Gln Ala Val Phe Ile Gly His Asp Trp Ala Gly
                325                 330                 335

Val Leu Val Trp Asn Met Ala Leu Phe His Pro Glu Arg Val Arg Ala
            340                 345                 350

Val Ala Ser Leu Asn Thr Pro Leu Met Pro Pro Asn Pro Glu Val Ser
        355                 360                 365

Pro Met Glu Val Ile Arg Ser Ile Pro Val Phe Asn Tyr Gln Leu Tyr
    370                 375                 380

Phe Gln Glu Pro Gly Val Ala Glu Ala Glu Leu Glu Lys Asn Met Ser
385                 390                 395                 400

Arg Thr Phe Lys Ser Phe Arg Thr Ser Asp Met Gly Leu Leu
                405                 410                 415

Thr Val Asn Lys Ala Thr Glu Met Gly Gly Ile Leu Val Gly Thr Pro
                420                 425                 430

Glu Asp Pro Lys Val Ser Lys Ile Thr Thr Glu Glu Ile Glu Tyr
            435                 440                 445

Tyr Ile Gln Gln Phe Lys Lys Ser Gly Phe Arg Gly Pro Leu Asn Trp
    450                 455                 460

Tyr Arg Asn Thr Glu Arg Asn Trp Lys Trp Ser Cys Lys Ala Leu Gly
465                 470                 475                 480

Arg Lys Ile Leu Val Pro Ala Leu Met Val Thr Ala Glu Lys Asp Ile
                485                 490                 495

Val Leu Arg Pro Glu Met Ser Lys Asn Met Glu Asn Trp Ile Pro Phe
            500                 505                 510

Leu Lys Arg Gly His Ile Glu Asp Cys Gly His Trp Thr Gln Ile Glu
        515                 520                 525

Lys Pro Ala Glu Val Asn Gln Ile Leu Ile Lys Trp Leu Lys Thr Glu
    530                 535                 540

Ile Gln Asn Pro Ser Val Thr Ser Lys Ile
545                 550

<210> SEQ ID NO 41
<211> LENGTH: 321
<212> TYPE: PRT
<213> ORGANISM: Solanum tuberosum

<400> SEQUENCE: 41

Met Glu Lys Ile Glu His Lys Met Val Ala Val Asn Gly Leu Asn Met
1               5                   10                  15

His Ile Ala Glu Leu Gly Gln Gly Pro Thr Ile Leu Phe Ile His Gly
            20                  25                  30

Phe Pro Glu Leu Trp Tyr Ser Trp Arg His Gln Met Val Tyr Leu Ala
        35                  40                  45

Glu Arg Gly Tyr Arg Ala Val Ala Pro Asp Leu Arg Gly Tyr Gly Asp
    50                  55                  60

Thr Thr Gly Ala Pro Ile Asn Asp Pro Ser Lys Phe Ser Ile Phe His
65                  70                  75                  80

Leu Val Gly Asp Val Val Ala Leu Leu Glu Ala Ile Ala Pro Asn Glu
                85                  90                  95

Asp Lys Val Phe Val Val Ala His Asp Trp Gly Ala Leu Ile Ala Trp
            100                 105                 110

His Leu Cys Leu Phe Arg Pro Asp Lys Val Lys Ala Leu Val Asn Leu
        115                 120                 125

Ser Val His Tyr His Pro Arg Asn Ser Asn Met Asn Pro Ile Glu Gly
    130                 135                 140
```

```
Leu Lys Ala Leu Tyr Gly Glu Asp Tyr Tyr Ile Cys Arg Phe Gln Val
145                 150                 155                 160

Pro Gly Glu Ile Glu Ala Glu Phe Ala Pro Ile Gly Ala Lys Ser Val
                165                 170                 175

Leu Lys Lys Met Leu Thr Tyr Arg Asp Pro Ala Pro Phe Tyr Phe Pro
            180                 185                 190

Lys Gly Lys Gly Leu Glu Ala Ile Ala Asp Ala Pro Ile Val Leu Ser
                195                 200                 205

Thr Trp Leu Ser Glu Glu Leu Asp Tyr Tyr Ala Asn Lys Phe Glu
    210                 215                 220

Gln Thr Gly Phe Thr Gly Ala Leu Asn Tyr Tyr Arg Ala Leu Ser Ile
225                 230                 235                 240

Asn Ser Glu Leu Thr Ala Pro Trp Thr Gly Ala Gln Val Asn Val Pro
                245                 250                 255

Thr Lys Phe Ile Val Gly Glu Phe Asp Leu Ala Tyr His Met Arg Gly
                260                 265                 270

Ala Lys Glu Tyr Ile His Asn Gly Gly Phe Lys Lys Tyr Val Pro Leu
                275                 280                 285

Leu Glu Glu Val Val Val Leu Glu Gly Ala Ala His Phe Val Asn Gln
    290                 295                 300

Glu Arg Pro His Glu Ile Ser Lys His Ile Tyr Asp Phe Ile Gln Lys
305                 310                 315                 320

Phe

<210> SEQ ID NO 42
<211> LENGTH: 341
<212> TYPE: PRT
<213> ORGANISM: Glycine max

<400> SEQUENCE: 42

Met Cys Glu His Leu Leu Val Ser Leu Ser Cys Tyr Ile Trp Val Arg
1               5                   10                  15

Thr Gln Arg Ile Val Glu Phe Asn Glu Met Glu Gln Ile Lys His Arg
                20                  25                  30

Thr Val Glu Val Asn Gly Ile Lys Met His Val Ala Glu Lys Gly Glu
            35                  40                  45

Gly Pro Val Val Leu Phe Leu His Gly Phe Pro Glu Leu Trp Tyr Ser
    50                  55                  60

Trp Arg His Gln Ile Leu Ser Leu Ser Ser Leu Gly Tyr Arg Ala Val
65                  70                  75                  80

Ala Pro Asp Leu Arg Gly Tyr Gly Asp Thr Glu Ala Pro Pro Ser Ile
                85                  90                  95

Ser Ser Tyr Asn Cys Phe His Ile Val Gly Asp Leu Val Ala Leu Ile
                100                 105                 110

Asp Ser Leu Gly Val Gln Gln Val Phe Leu Val Ala His Asp Trp Gly
            115                 120                 125

Ala Ile Ile Gly Trp Tyr Leu Cys Met Phe Arg Pro Asp Lys Val Lys
130                 135                 140

Ala Tyr Val Cys Leu Ser Val Pro Leu Leu Arg Arg Asp Pro Asn Ile
145                 150                 155                 160

Arg Thr Val Asp Gly Met Arg Ala Leu Tyr Gly Asp Asp Tyr Tyr Val
                165                 170                 175

Cys Arg Phe Gln Lys Pro Gly Glu Met Glu Ala Gln Met Ala Glu Val
                180                 185                 190
```

```
Gly Thr Glu Tyr Val Leu Lys Asn Ile Leu Thr Thr Arg Asn Pro Gly
            195                 200                 205

Pro Pro Ile Leu Pro Lys Gly Arg Phe Gln Phe Asn Pro Glu Met Pro
210                 215                 220

Asn Thr Leu Pro Ser Trp Leu Thr Glu Glu Asp Leu Ala Tyr Tyr Val
225                 230                 235                 240

Ser Lys Phe Glu Lys Thr Gly Phe Thr Gly Pro Leu Asn Tyr Tyr Arg
            245                 250                 255

Asn Phe Asn Leu Asn Trp Glu Leu Thr Ala Pro Trp Thr Gly Gly Gln
            260                 265                 270

Ile Lys Val Pro Val Lys Tyr Ile Thr Gly Glu Leu Asp Met Val Tyr
            275                 280                 285

Asn Ser Leu Asn Leu Lys Glu Tyr Ile His Gly Gly Phe Lys Gln
290                 295                 300

Asp Val Pro Asn Leu Glu Gln Val Ile Val Lys Gly Val Ala His
305                 310                 315                 320

Phe Asn Asn Gln Glu Ala Ala Glu Glu Ile Asp Asn Tyr Ile Tyr Asp
                    325                 330                 335

Phe Ile Asn Lys Phe
            340

<210> SEQ ID NO 43
<211> LENGTH: 330
<212> TYPE: PRT
<213> ORGANISM: Bradyrhizobium japonicum

<400> SEQUENCE: 43

Met Gly Glu Pro Thr Gln Arg Thr Ile Lys Ala Asn Gly Ile Ser Leu
1               5                   10                  15

Asn Val Ala Glu Gln Gly Lys Gly Pro Met Val Leu Leu Cys His Gly
                20                  25                  30

Phe Pro Glu Gly Trp Tyr Ser Trp Arg His Gln Leu Glu Ala Leu Ala
            35                  40                  45

Ala Ala Gly Tyr His Ala Val Ala Pro Asp Met Arg Gly Tyr Gly Lys
        50                  55                  60

Ser Asp Arg Pro Glu Ala Ile Asp Gln Tyr Thr Ile Leu His Met Val
65                  70                  75                  80

Gly Asp Leu Val Gly Val Leu Asp Ala Phe Glu Val Lys Asp Ala Val
                85                  90                  95

Ile Val Gly His Asp Trp Gly Ala Thr Ile Ala Trp Thr Ala Arg
            100                 105                 110

Leu Arg Pro Asp Arg Phe Arg Ala Ala Ile Leu Ser Val Pro Tyr
            115                 120                 125

Arg Pro Arg Ser Glu Ala Arg Pro Thr Ser Val Met Pro Gln Thr Ala
130                 135                 140

Asp Ala Gln Phe Tyr Gln Leu Tyr Phe Gln Glu Pro Val Ala Glu
145                 150                 155                 160

Ala Glu Phe Glu Arg Asp Pro Arg Ala Thr Leu Gly Ala Met Leu Tyr
                165                 170                 175

Gly Gly Ser Gly Glu Gly Ala Ala Ile Arg Ala Ser Ala Glu Arg
            180                 185                 190

Ala Gly Arg Thr Val Gly Val Gly Met Val Ser Arg Lys Asp Gly Met
            195                 200                 205

Leu Pro Lys Val Gln Val Pro Leu Pro Ser Trp Leu Ser Ala Thr Asp
210                 215                 220
```

-continued

```
Leu Asp Tyr Tyr Ser Ala Glu Phe Ala Arg Ser Gly Phe Arg Gly Pro
225                 230                 235                 240

Leu Asn Tyr Tyr Arg Asn Ile Asp Arg Asn Trp Glu Leu Met Gly Ala
                245                 250                 255

Phe Glu Gly Val Lys Val Val Val Pro Ser Leu Phe Ile Ala Gly Asp
            260                 265                 270

His Asp Met Val Ile Ala Phe Pro Gly Ala Ala Glu His Leu Ala Asn
        275                 280                 285

Met Lys Gln Phe Val Pro Gln Leu Arg Glu Ile Lys Ile Leu Pro Gly
    290                 295                 300

Cys Gly His Trp Thr Gln Gln Glu Arg Pro Thr Glu Val Asn Ala Ala
305                 310                 315                 320

Ile Val Glu Phe Leu Arg Ser Leu Pro Gly
                325                 330
```